(12) United States Patent
Maurel et al.

(10) Patent No.: US 11,278,568 B2
(45) Date of Patent: Mar. 22, 2022

(54) IN SITU PREPARATION OF CYANO-BRIDGED METAL NANOPARTICLES WITHIN A BIOCOMPATIBLE REVERSE MICELLAR SYSTEM

(71) Applicants: MEDESIS PHARMA, Baillargues (FR); CENTRE NATIONAL DE LA RECHERCHE SCIENTIFIQUE, Paris (FR); UNIVERSITE DE MONTPELLIER, Montpellier (FR)

(72) Inventors: Jean-Claude Maurel, Castries (FR); Elsa Compte, Montpellier (FR); Cyril Lavaud, Montpellier (FR); Yannick Guari, Prades-le-lez (FR); Joulia Guari, Prades-le-lez (FR); Jérôme Long, Montpellier (FR)

(73) Assignees: MEDESIS PHARMA, Baillargues (FR); CENTRE NATIONAL DE LA RECHERCHE SCIENTIFIQUE, Paris (FR); UNIVERSITE DE MONTPELLIER, Montpellier (FR)

( * ) Notice: Subject to any disclaimer, the term of this patent is extended or adjusted under 35 U.S.C. 154(b) by 0 days.

(21) Appl. No.: 15/742,719

(22) PCT Filed: Jul. 8, 2016

(86) PCT No.: PCT/EP2016/066269
§ 371 (c)(1),
(2) Date: Jan. 8, 2018

(87) PCT Pub. No.: WO2017/005899
PCT Pub. Date: Jan. 12, 2017

(65) Prior Publication Data
US 2018/0200295 A1 Jul. 19, 2018

(30) Foreign Application Priority Data

Jul. 9, 2015 (EP) .................................. 15306135

(51) Int. Cl.
| | |
|---|---|
| *A61K 33/32* | (2006.01) |
| *A61K 9/107* | (2006.01) |
| *A61K 31/28* | (2006.01) |
| *A61K 9/51* | (2006.01) |
| *A61K 47/28* | (2006.01) |
| *A61K 31/26* | (2006.01) |
| *A61K 47/10* | (2017.01) |
| *A61K 9/00* | (2006.01) |
| *A61K 33/26* | (2006.01) |
| *A61K 33/30* | (2006.01) |
| *A61K 47/24* | (2006.01) |

(52) U.S. Cl.
CPC .............. *A61K 33/32* (2013.01); *A61K 9/006* (2013.01); *A61K 9/1075* (2013.01); *A61K 9/5192* (2013.01); *A61K 31/26* (2013.01); *A61K 31/28* (2013.01); *A61K 33/26* (2013.01); *A61K 33/30* (2013.01); *A61K 47/10* (2013.01); *A61K 47/24* (2013.01); *A61K 47/28* (2013.01)

(58) Field of Classification Search
None
See application file for complete search history.

(56) References Cited

U.S. PATENT DOCUMENTS

| | | | |
|---|---|---|---|
| 2010/0215587 A1* | 8/2010 | Huang | A61K 49/0002 424/9.36 |
| 2010/0266676 A1 | 10/2010 | Saulnier et al. | |
| 2013/0052279 A1* | 2/2013 | Maurel | A61P 25/28 424/639 |
| 2013/0065944 A1* | 3/2013 | Maurel | A61K 9/1272 514/44 A |
| 2014/0194665 A1* | 7/2014 | Ishii | G21F 9/12 588/6 |
| 2015/0050347 A1 | 2/2015 | Maurel | |
| 2017/0035909 A1* | 2/2017 | Bauer | A61P 39/02 |

FOREIGN PATENT DOCUMENTS

| | | |
|---|---|---|
| EP | 1652512 A1 | 5/2006 |
| EP | 1652513 A1 | 5/2006 |
| EP | 2116511 A1 | 11/2009 |
| WO | WO 96/23811 A1 | 8/1996 |

(Continued)

OTHER PUBLICATIONS

J. Nesamony et al., "IPM/DOSS/Water Microemulsions as Reactors for Silver Sulfadiazine Nanocrystal Synthesis," Journal of Pharmaceutical Sciences, vol. 94, 1310-1320 (2005).*
"What is Deionized Water or Di Water?" Total Water, <https://www.total-water.com/blog/deionized-water-di-water/>, published Dec. 22, 2014, p. 1-2.*
M. Shokouhimehr et al., "Dual purpose Prussian blue nanoparticles for cellular imaging and drug delivery: a new generation of T1-weighted MRI contrastand small molecule delivery agents," Journal of Materials Chemistry, 2010, 20, pp. 5251-5259.*
International Search Report and Written Opinion issued in International Patent Application No. PCT/EP2016/066269, dated Sep. 6, 2016 (11 pages).

(Continued)

*Primary Examiner* — Nannette Holloman
(74) *Attorney, Agent, or Firm* — Arent Fox LLP

(57) ABSTRACT

The present invention relates to a method for in situ preparation of cyano-bridged coordination polymers as metal nanoparticles within a biocompatible reverse micellar system by mixing at least two reverse micellar systems, each one containing at least one metal salt precursor. The invention also relates to the stabilization of theses nanoparticles by using a biocompatible reverse micellar system. This system takes part of the synthesis as a nanoreactor which comprises at least an acylglycerol, a sterol, lecithin, ethanol and water for the preparation of stable cyano-bridged metal nanoparticles without any use of additional stabilizer agent.

20 Claims, 5 Drawing Sheets

(56) References Cited

FOREIGN PATENT DOCUMENTS

WO    2015124581 A1    8/2015

OTHER PUBLICATIONS

Vaucher et al., "Synthesis of Prussian Blue Nanoparticles and Nanocrystal Superlattices in Reverse Microemulsions," Angew. Chem. vol. 112(10), 2000, pp. 1863-1866.

\* cited by examiner

IN SITU PREPARATION OF CYANO-BRIDGED METAL NANOPARTICLES WITHIN A BIOCOMPATIBLE REVERSE MICELLAR SYSTEM

CROSS REFERENCE TO RELATED APPLICATIONS

This application is a 35 U.S.C. 371 National Phase of PCT Application No. PCT/EP2016/066269 filed Jul. 8, 2016, which claims benefit to EP Application No. 15306135.3 filed Jul. 9, 2015, the disclosure of which is hereby incorporated by reference in its entirety.

The present invention relates to a method for in situ preparation of cyano-bridged coordination polymers as metal nanoparticles within a biocompatible reverse micellar system by mixing at least two reverse micellar systems, each one containing at least one metal salt precursor. The invention also relates to the stabilization of theses nanoparticles by using a biocompatible reverse micellar system. This system takes part of the synthesis as a nanoreactor which comprises at least an acylglycerol, a sterol, lecithin, ethanol and water for the preparation of stable cyano-bridged metal nanoparticles without any use of additional stabilizer agent.

BACKGROUND OF THE INVENTION

Cyano-bridged coordination polymers belong to an important family of magnetic molecular-based materials. These materials exhibit a range of compounds with wide interests for their magnetism (Holmes, 1999), electro- and photo-chromism (Sato, 2003 and Sato, 2007), heavy-metal sequestration (Torad, 2012) and spin-crossover effects (Papanikolaou, 2007).

One of the most important cyano-bridged compound is the Prussian Blue (refers as PB). PB comprises Iron (III) linked to ferrohexacyanide anions, well studied since its discovery by Dippel and Diesbach in the early 1700s. The first structural hypothesis postulates the occurrence of interstitial metal ions within the cubic face-centered unit cell (Keggin, 1936). This hypothesis leads to a unit cell containing 4/3 formula unit of $Fe_4[Fe(CN)_6]_3$ where 4 ferrocyanides are octahedral, 4 Iron (III) are linked to the nitrogen of the cyanide, and 4/3 ferric ions are distributed in an eightfold interstitial position. Then, this cubic face-centered unit cell was confirmed by Ludi and Buser, however they showed a more complicated structure with randomly distributed vacancies by X-ray techniques (Ludi, 1970 and Buser, 1972).

Central Iron can be replaced by transition metal cations to form related cyano-metalate-based coordination polymers known as Prussian Blue Analogs (refers as PBA). PBA can be synthesized by the traditional mixture of two water solutions, one containing hexacyano-metalates anions $[M'(CN)_6]^{q-}$ with another containing transition metal Lewis acids $M^{p+}$ which leads to bulk compounds comprising a neutral three-dimensional networks $M_p[M'(CN)_6]_q$, $nH_2O$.

Actually, this formula does not take into account the presence of intrinsic vacancies and the presence of an alkali metal cation to counter the charge of the cyano-metalate anion. Therefore, the formula should be written as $A_{4x}M_4[M'(CN)_6]_{4z}\square_{4(1-z)}, nH_2O$, where A is an alkali metal cation and $\square$ a vacancy (Verdaguer, 2004). In addition to the formula above, the number of CN groups can range from 4 to 8 depending on the transition metal bonded to the cyano-metalate anion. Certain properties of cyano-bridged coordination polymers can be attributed to the presence of these vacancies which can be filled by many atoms depending on adsorption's diffusion (Kaye, 2006).

The main application of PB compounds concerns cesium decorporation. After Chernobyl accident, first treatments consisted in oral administrations of PB capsules (of 3 to 10 grams) to contaminated humans. Known as Radiogardase®, PB compounds were colloidal particles in aqueous phase with sizes ranging from 10-100 microns. The PB particles remain in the digestive tract and absorb cesium in their interstitial vacancies. A large PB particles quantity must be constant into the digestive tract to inhibit the re-absorption of cesium which follows the potassium path (known as enterohepatic circulation). At equimolar concentrations, cesium atoms are linked to PB particles with superior efficiency compared to sodium and potassium ($10^3$ to $10^4$ times superior according to IAEA—International Atomic Energy Agency—in 1997). Besides, once cesium atoms are absorbed by interstitial vacancies of PB, the insoluble particles are excreted within urine and feces according to HPA—Health Protection Agency—in 2010.

However, the use of large quantities of PB may cause unwanted side effects, such as:
Low efficiency of treatment for children (43%)
Hypokalemia: heart troubles (Farina, 1991);
Severe constipation: dangerous cesium exposition in the intestinal lumen (Stevens, 1974); and/or
Abdominal pain (according to the FDA).

Thus there is a need for a novel therapy that would avoid theses side effects and improve the decorporation treatment for mammals, non-human or human mammals, and more specifically for children.

Recently, these cyano-bridged coordination polymers have been studied within the nanometric scale. Nanoparticles investigations spread drastically due to novel crystal properties which differ from the bulk compounds (Klabunde, 2001 and Larionova, 2009). Because the optical, electrical, magnetic, chemical and biomedical properties of inorganic metal nanoparticles are widely dependent on the size, shape, composition and structure, drastic efforts have been devoted to the synthesis medium. For instance, PB and PBA can be synthesized with new methods such as polymer protection (Li, 2006), Langmuir-Blodgett (Wang, 2007), sol-gel (Guo, 1999) and ionic liquids (Clavel, 2006). In particular, nanoparticles formed in water need a long-chain polymer to protect them from growing and by the way to control their size (Yamada, 2004 and Chelebaeva, 2008).

The use of reverse micellar system is one of methods for the preparation of nanoparticles. Indeed, the water droplets contained in an organic phase produce a homogenous isotropic phase and provide nanoreactors for the synthesis of various inorganic nanostructures. This method allows a control over the particle scale and nano-architecture and provides precursors confinement to form nanoparticles stabilized by the microemulsion itself (Pileni, 1997 and 2007 and Qi, 2006).

In general, a microemulsion is a system comprising water, oil, and amphiphilic compounds which is an optically isotropic and thermodynamically stable liquid phase (Danielsson, 1981). The amphiphilic compounds can self-assemble into a huge variety of organized structures in liquid, such as direct and reverse micelles respectively oil-in-water (o/w) and water-in-oil (w/o) microemulsions, vesicles and lyotropic liquid crystals. Other compounds can be added to form microemulsions, depending on the size range and stability of micelles needed, and are called co-surfactants (Saito, 1967). In the case of nanoparticles synthesis, the nature of each component is important to give a stable system.

Characteristics of nanoparticles synthesized by the w/o microemulsion reaction method depends on many variables such as aqueous phase content, component concentration, nature of solvent, surfactant and the necessary addition of a co-surfactant to enhance stability and homogeneity of the microemulsion (Eastoe, 2006). The general method to synthesize nanoparticles comprises a mixture of two reverse micellar systems both containing a metal precursor (Lopez-Quintela, 2003). The nanoparticles are formed by the means of the intermicellar exchange at different rates depending on the compounds concentration.

Over all the various surfactants used in microemulsion formulations, the most popular are the ionic surfactants—such as the double-chained surfactant sodium bis(2-ethylhexyl)sulfosuccinate (refers as AOT) the cetyltrimethylammonium bromide (refers as CTAB)—and nonionic polyethoxylated surfactants (Barnickel, 1990, Pileni, 1993 and Lopez-Quintila, 2003b).

In particular, Vaucher and co-workers (Vaucher, 2000) synthesized PB nanoparticles in reverse microemulsion comprising AOT and isooctane. A small amount of the $(NH_4)_3[Fe(C_2O_4)_3]$ and $(NH_4)_3[Fe(CN)_6]$ equimolar mixture was added to the microemulsion at room temperature in the dark to form the w/o microemulsion. Then, the microemulsions were exposed to daylight in order to slowly photoreduce the oxalate ions and synthesize the PB nanoparticles. The main issue is to determine the various factors which control the size of the PB crystals. They thus described Transmission Electron Microscopy (refers as TEM) images showing the presence of cubic PB nanoparticles with a size range varying from 12 to 54 nm.

Later, Li and co-workers (Li, 2004) synthesized in the same reverse microemulsion PB nanoparticles type. However, they used a polymer to protect PB nanoparticles allowing a better control over the size. They proceeded using AOT in isooctane where first, an aqueous solution of $FeCl_2$ and polyvinylpyrrolidone (PVP) is added to the oil phase, second, an aqueous solution of $K_3Fe(CN)_6$ is added to another oil phase. Then, the equal volumes of the former two microemulsions were mixed. The results showed that the PVP acted as steric stabilizer for the nucleation and growth of PB. They characterized nanoparticles with a size range from 20 to 27 nm.

Unfortunately, AOT and CTAB surfactants give rise to a high toxicity towards aquatic organisms, living subjects and pollute the environment (Okumura, 1998). In the reverse micellar systems, not only surfactants have toxicity but dispersive liquids such as oils and hydrocarbons have no viable biocompatibility. Main oils used in reverse micellar system comprise long chains carbons such as hexane, octane and decane (Fletcher, 1987, Atik, 1981, Pileni, 1997 and Eastoe, 2006).

Nesamony and coworkers (Nesamony, 2005) used pharmaceutically acceptable components such as the isopropyl myristrate solvent (IPM) and the dioctyl sodium sulfosuccinate surfactant (DOSS) to form nanocrystals of silver sulfadiazine in a water in oil microemulsion for antimicrobial uses. Two reverse micellar phases are prepared—the first containing $AgNO_3$ and the second containing sodium sulfadiazine (NaSD) in the aqueous droplets—and mixed together to form silver sulfadiazine (AgSD) nanoparticles at room temperature. The authors produced submicron nanoparticles with a concentration greater than its solubility. However, the nanoparticles are inherently unstable and the authors suggest using an acceptable coating/capping reagent to inhibit the particle growth.

Ma and coworkers (Ma, 2010) used an amphiphilic micellar system which comprises lipids and polyethyleneglycols to form encapsulated manganese iron oxide. Actually, the $MnFe_2O_4$ nanocrystals are synthesized alone in organic phase at high temperature. Then, these nanocrystals are dispersed within the lipids-polyethyleneglycols phase and the mixture is added into water with sonication. However, the nanoparticles are encapsulated by the amphiphilic lipid surfactant without an aqueous phase within the core of micelles and it is intravenously administrated.

Noritomi and coworkers (Noritomi, 2013) prepared silver nanoparticles using reverse micelles of sucrose fatty acid esters such as alkylglucosides. The preparation of nanoparticles consists in mixing equal volume of two reverse micellar phases at room temperature and at the same water content: the first phase containing $AgNO_3$ and the second containing hydrazine or sodium borohydride. They observed nanoparticles with a mean diameter of 14 nm, stabilized at least one month at room temperature. However, this work highlighted the great influence of lots of parameters, such as temperature, water content, and type of reactants, in order to synthesize monodisperse nanoparticles with same shape and size.

The above cited documents highlight the influence of several parameters on the preparation of stable nanoparticles within a microemulsion. It also confirms the difficulty to obtain a stable reverse micellar system depending on the desired nature of nanoparticles.

Furthermore, biocompatible microemulsions comprising cyano-bridged metal nanoparticles have not been described so far. Such nanoparticles were synthesized by other ways depending on the final applications.

For instance, Huang and coworkers, (US 2010/0254912 A1) used PB nanomaterials as Magnetic Resonance Imaging (refers as MRI) agents synthesized in water solutions, and stabilized by carboxylic acids. This reference relates to all the PBA and use of Gadolinium doped PB nanoparticles. The synthesis of said nanoparticles was performed by slow addition of an aqueous solution containing iron chloride and gadolinium chloride to an aqueous solution of hexacyanoferrate. The two aqueous solutions contain citric acid which is used as a carboxylic surface-capping agent to control the nanoparticles size (size range of 5 to 300 nm) and prevent the nanoparticles agglomeration.

In a similar way, Perrier and coworkers investigated Nuclear Magnetic Resonance (refers as NMR) relaxivity of nano-sized cyano-bridged particles synthesized in aqueous solution and stabilized with organic polymers compound (Perrier, 2013). An aqueous solution of $K_3[M(CN)_6]$ containing the appropriate amount of stabilizer was mixed with a $Ln(NO_3)_3,nH_2O$ solution containing the same amount of stabilizer. The stabilizers used comprise mainly PEG-types polymers which are considered biocompatible and allow to form cyano-bridged metal nanoparticles with size range of 2 to 3.4 nm. More recently, Zhu and coworkers (Zhu, 2015) studied the synthesis of Mn-doped PB with the use of PEGylated compounds in order to exhibit optical and magnetic properties. They found that the presence of Mn in PB enhances the tumor imaging.

These three documents disclose biocompatible organic compounds suitable for intravenous administration with aqueous solution.

Grandjean and coworkers (WO 2010/133689 A2) prepared solid hexa- and octacyanometalate nanocomposite material as a graft on an organic group chemically bonded to the pores cores of a porous glass medium. They also used another medium such as a functionalized supported membrane to graft cyano-bridged metal nanoparticles (WO 2014/049048 A1). Both patents concern the cesium recovery from a polluted nuclear effluent and cannot therefore be readily transferred to human decorporation.

The above cited documents evidenced that stabilizing agents are necessary to prepare size-controlled cyano-bridged metal nanoparticles or matrices able to obtain grafted cyano-bridged metal nanoparticles.

There is thus a need for cyano-bridged metal nanoparticles prepared and stabilized within a biocompatible microemulsion which acts as the reactor medium.

In addition, the medium should allow the nanoparticles to be transported to organic tissues.

The applicant discloses the use of a reverse-micellar system based on acylglycerols, phospholipids or sphingolipids and metal cations as active substances (WO 2011/117333). Said reverse micellar systems are able to cross mucosa and cellular membranes and thus allow vectorization of metal cations, as active ingredients, to target sites.

Actually, use of non-toxic cyano-bridged metal nanoparticles within a biocompatible reverse micellar system capable of transmucosal delivery, and/or capable of being orally administered, does not exist yet at this point.

The Applicant surprisingly evidenced here that cyano-bridged metal nanoparticles can be prepared in a reverse micellar system and thus be driven efficiently to target tissues or sites (such as gastrointestinal tract) without any need for organic polymers acting as stabilizer agents or protecting agents during their preparation and uses. The reverse micellar system acts both as a reactor medium and as a protecting shell for the in situ prepared cyano-bridged metal nanoparticles allowing stabilization over six months. Then, the reverse micellar system acts as a vector for delivery of the cyano-bridged metal nanoparticles to the desired cells and/or organs.

SUMMARY OF THE INVENTION

A first object of the invention is a method for the preparation of biocompatible reverse micellar system comprising cyano-bridged metal nanoparticles, wherein said method comprises the following step consisting of:

mixing (i) at least one biocompatible reverse micellar system comprising at least one acylglycerol, sterol, lecithin, ethanol, and an aqueous solution comprising at least one metal salt, and water, with (ii) a biocompatible reverse micellar system comprising at least one acylglycerol, a sterol, lecithin, ethanol, and an aqueous solution comprising a cyano-metalate salt, and water.

Another object of the invention is a biocompatible reverse micellar system comprising at least one acylglycerol, a sterol, lecithin, ethanol, cyano-bridged metal nanoparticles and water, said system does not comprise any stabilizing agent. More specifically, the cyano-bridged metal nanoparticles comprised in the biocompatible reverse micellar system according to the invention are advantageously stabilized by the reverse micellar system without any need for a specific stabilizing agent.

Another object of the invention is a biocompatible reverse micellar system comprising at least one acylglycerol, a sterol, lecithin, ethanol, cyano-bridged metal nanoparticles and water, wherein said system does not comprise any stabilizing agent, and wherein the biocompatible reverse micellar system or the cyano-bridged metal nanoparticles comprised therein are used as a contrast agent and/or as a diagnosis agent.

Another object of the invention is a biocompatible reverse micellar system comprising at least one acylglycerol, a sterol, lecithin, ethanol, cyano-bridged metal nanoparticles and water, wherein said system does not comprise any stabilizing agent, and wherein the biocompatible reverse micellar system or the cyano-bridged metal nanoparticles comprised therein are used for substitution by and/or sequestering of radionuclide and/or metal cations.

Another object of the invention is a composition comprising biocompatible reverse micellar systems of the invention.

DETAILED DESCRIPTION OF THE INVENTION

Figure 1:
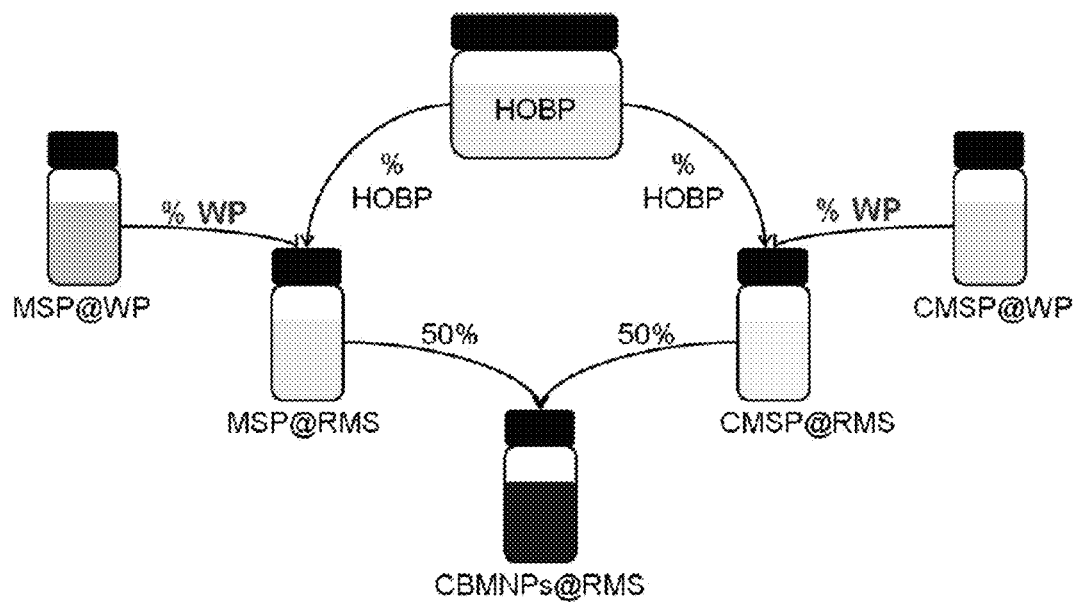
FIG. 1: Schematic overview of the steps for in situ synthesis of the PB nanoparticles within a reverse micellar system, HOBP stands for Homogenous Oil-Based Phase, MSP stands for Metal Salt Precursor, WP stands for Water Phase, CMSP stands for Cyano-Metalate Salt Precursor, RMS stands for Reverse Micellar System and CBMNPs stand for Cyano-Bridged Metal NanoParticles.

A first object of the invention is a method for the in situ preparation of cyano-bridged coordination polymers as nanoparticles within a biocompatible reverse micellar system.

The term "cyano-bridged coordination polymer" refers to repetition of successive assembling of metallic cation $M^{p+}$ and cyano-metalate anions $[M'(CN)_n]^{q-}$ obtained by growth of a cyano-bridged network (comprising CN ligands) within the reverse micellar system. Generally, said polymers form a network of polymers. This polymer is named as a coordination polymer when a metal precursor M is linked to another metal precursor M' by the CN ligand to form the subunit M'-CN-M, such subunit is repeated many times in the reactor medium.

The present method comprises the following step consisting of:

mixing (i) at least one biocompatible reverse micellar system comprising at least one acylglycerol, sterol, lecithin, ethanol, an aqueous solution comprising at least one metal salt, as a precursor, and water, with (ii) a biocompatible reverse micellar system comprising at least one acylglycerol, a sterol, lecithin, ethanol, an aqueous solution comprising at least one cyano-metalate salt, as a precursor, and water.

According to the invention, the metal salt refers to a metallic cation with generally chloride or nitric anions as counter-anions and water molecules. Preferably, the counter-anion is chloride. The metallic cation ($M^{p+}$) can be chosen among transition metals and lanthanides cations. The metallic cations may have one or more positive charges (p+), p is generally an integer from 1-10, more specifically p is 2, 3, 4, or 5, and the number of counter-anions and water molecules depends on the number of positive charges.

Transition metals cations (referred as M) used can be chosen among all the existing transition metals cations. The transition metals cations used according to the invention are iron, zinc, and manganese. Preferably, the transition metal cation used in the invention is iron.

Lanthanides cations (also referred as M) can be chosen among all the existing lanthanides cations, including gadolinium (Gd), terbium (Tb), or ytterbium (Yb). The lanthanide cation more particularly used according to the invention is gadolinium.

More specifically, the metallic cation ($M^{p+}$) can be iron ($Fe^{2+}$ or $Fe^{3+}$), zinc ($Zn^{2+}$), manganese ($Mn^{2+}$) or gadolinium ($Gd^{3+}$), which forms respectively $FeCl_2,4H_2O$; $FeCl_3,6H_2O$; $ZnCl_2,4H_2O$; $MnCl_2,4H_2O$; or $Gd(NO_3)_3, 6H_2O$.

The aqueous solution comprising at least one metal salt can comprise one, two or three metal salt(s) (i.e. one metal salt or a mixture of metal salts).

According to the invention, the cyano-metalate salt ($Alk^+_x[M'(CN)_n]^{q-}$) refers to a metallic cation (M') with generally CN ligands and alkali cations ($Alk^+$). The metallic cation (M') can be chosen among transition metals cations, which lead to the number of CN ligands and alkali cations linked thereto, q is generally an integer, equals to x, more specifically q is 2, 3, or 4; and n is generally an integer, more specifically n is 4, 6 or 8; and x is generally an integer, more specifically x is 2, 3, or 4.

More specifically, the metallic cation (M') can be iron ($Fe^{2+}$ or $Fe^{3+}$), cobalt ($Co^{2+}$ or $Co^{3+}$), nickel ($Ni^{2+}$), molybdenum ($Mo^{4+}$, $Mo^{5+}$) or tungsten ($W^{4+}$). M' is preferably iron.

The alkali cation ($Alk^+$) can be lithium ($Li^+$), rubidium ($Ru^+$), sodium ($Na^+$), potassium ($K^+$) or cesium ($Cs^+$) (in the case of decorporation). Sodium cation is more preferred when the cyano-bridged metal nanoparticles are for use in the medical and pharmaceutical fields.

The formula $Alk^+_x[M'(CN)_n]^{q-}$ can be the following: $Na_4[Fe(CN)_6]$, $Na_3[Fe(CN)_6]$, $Na_2[Ni(CN)_4]$, $Na_4[Mo(CN)_8]$, or $Na_4[W(CN)_8]$. Sodium can be replaced by potassium in the previous formulas.

Accordingly, the mixing of the method of the invention allows an in situ synthesis of the cyano-bridged metal nanoparticles in the reverse micellar system.

Generally, the amounts of metal salts and cyano-metalate salts in the biocompatible reverse micellar systems (i) and (ii) can vary in a large extent. The amounts of the biocompatible reverse micellar systems (i) and (ii) to be mixed can also vary in a large extent. In specific embodiments, mixing of said (i) and (ii) biocompatible reverse micellar systems is carried out in such a way that the metal salts and the cyano-metalate salts are in equivalent molar amounts.

According to specific embodiments, the (i) at least one biocompatible reverse micellar system can comprise one or more (such as 2 or 3) metal salts.

According to other embodiments, the (i) at least one biocompatible reverse micellar system can be one, two or three biocompatible reverse micellar systems, each comprising a metal salt different from the other. Accordingly, the biocompatible reverse micellar systems (i) comprising at least one metal salt can be mixed altogether with the biocompatible reverse micellar systems comprising at least one cyano-metalate salt (ii).

The term "biocompatible" system refers to the compatibility with living cells, tissues, organs or systems; more specifically it refers to a system that poses no risk of injury, toxicity or rejection by the immune system of mammals, and more preferably human mammals.

The conditions for mixing, more specifically time and temperature, can be readily determined by any one skilled in the art. In practice, the temperature may vary from room temperature (18-25° C.) to 40° C. in an atmospheric pressure. The time for mixing is such that a homogenous reverse micellar system is obtained, and more specifically a visually limpid formulation is obtained.

According to particular embodiment, prior to mixing, said (i) and (ii) biocompatible reverse micellar systems can be prepared by a method comprising the following steps:

Step 1: separate preparation of aqueous solutions each containing at least one metal precursor (i.e., at least one aqueous solution comprises at least one metal salt compound and the other one at least one cyano-metalate salt) by dissolving each metal precursor in water, preferably deionized water, Step 2: each of the aqueous solutions obtained by step 1 is solubilized within a homogenous oil-based phase comprising at least one acylglycerol, a sterol, lecithin, and ethanol, and optionally water, as to form a homogenous reverse micellar system, wherein said homogenous oil-based phases are preferably the same (in terms of quality and quantity, i.e., same compounds in the same amounts).

According to a preferred embodiment of Step 1, the metal precursors are dissolved in water in appropriate concentrations as to obtain the final nanoparticles concentration desired in the reverse micellar system. One skilled in the art will thus assess the quantities of the metal precursors to be dissolved as to get the desired final nanoparticles concentration. An aqueous solution is defined as a solution in which the solvent is substantially water. The word aqueous is defined as pertaining to, related to, similar to, or dissolved in water.

More specifically, the reverse micellar systems obtained by step 2 are the biocompatible reverse micellar systems (i)

and (ii) that are mixed together thereafter, according to the method of the invention, preferably the amount by weight of the biocompatible reverse micellar systems (i) is the same as the amount of the biocompatible reverse micellar system (ii). Said biocompatible reverse micellar systems are preferably the same (in terms of quality and quantity, i.e., same compounds in the same amounts), except for the metal precursors which are different in each biocompatible reverse micellar system.

More specifically, mixing according to the method of the invention allows the metal precursors to interact and induces therefore an in situ cyano-bridged metal nanoparticles formation within the obtained reverse micellar system.

The homogenous oil-based phase of the invention used at step (2) can be prepared by any technique known in the art. More particularly, they can be obtained by the following method:
(a) Contacting (i) acylglycerol, preferably diacylglycerol, (ii) lecithin, (iii) ethanol (iv) sterol, and (v) optionally water, preferably purified water,
(b) Stirring mixture obtained by step (a), at 40° C. or less, and for a time sufficient to obtain formation of homogenous oil-based phase.

The parameters of stirring, more specifically duration and speed of mechanical stirring, can be readily determined by any one skilled in the art and depend on experimental conditions. In practice, these parameters are such that a homogenous oil-based phase is obtained; the speed is determined so as to enable formation of a visually limpid formulation and duration of the stirring is such that the stirring may be stopped few minutes (e.g. 2, 3, 4, 5 or 6 minutes) after obtaining the visually limpid formulation.

The term "homogenous" phase or reverse micellar system refers to a system which is visually limpid.

An overview of the in situ preparation of specific cyano-bridged metal nanoparticles is shown in FIG. 1.

Generally, the method of the invention is carried out from room temperature (i.e. from 18° C. to 25° C.) to 40° C., except otherwise specified.

Components of the Homogenous Oil-Based Phases or Reverse Micellar Systems

Acylglycerols

Acylglycerols used in the reverse-micellar system or homogenous oil-based phases according to the invention can be isolated from the majority of animals, and more preferably plants.

Acylglycerols used according to the invention include mono-, di- and tri-acylglycerols of the following formula (I):
$CH_2(OR_1)$—$CH(OR_2)$—$CH_2(OR_3)$,
in which:
$R_1$ is an acyl residue of a linear or branched unsaturated fatty acid having between 14 and 24 carbons atoms;
$R_2$ is an acyl residue of a linear or branched unsaturated fatty acid having between 2 and 18 carbons atoms, or a hydrogen atom;
$R_3$ is an acyl residue of a linear or branched unsaturated fatty acid having between 14 and 24 carbons atoms, or a hydrogen atom.

According to a particular embodiment, $R_1$ or $R_3$, preferably only one of $R_1$ and $R_3$, in particular only $R_1$ represents an acyl residue of oleic acid (C18:1[cis]-9).

According to a particular aspect, $R_2$ has 18 carbon atoms, preferably $R_2$ is an oleic acid residue (oleoyl group), one of its positional isomers with respect to the double bond (cis-6,7,9,11 and 13) or one of its iso-branched isomers.

According to another particular aspect, R1 represents an oleoyl group.

According to another particular aspect, R3 is a hydrogen atom.

According to another particular aspect, R2 and R3 are hydrogen atoms.

As a general rule, oil containing a high concentration of oleic acid will be chosen as a useful source of acylglycerols according to the invention. Such oil usually contains a high proportion of acylglycerols useful according to the invention.

According to a particular aspect of the invention, the preferred acylglycerols are glycerol 1-monooleate and glycerol 1,2-dioleate.

A certain number of them, and more particularly those which are found to be the most active in the applications sought after, are also available commercially. For instance, glycerol monooleate 40 contains about 32 to 52% of monoacylglycerol, 30 to 50% of diacylglycerol, 5 to 20% of triacylglycerol and is pharmaceutically accepted (European Pharmacopeia (8th Edition), USP 25/NF20, and Japanese Standard of food Additives).

Such product is for instance commercially available by Gattefossé Company under the name Peceol®. In particular, Peceol® may comprise around 45.3 wt % of monoacyl glycerol, around 44.5 wt % of diacylglycerol and around 8.6 wt % of triacyl glycerol (the acyl fraction of Peceol® is mainly made of oleoyl—usually around 80% of the acyl residue is oleoyl fraction).

According to the present description, the weight of acylglycerol corresponds to the total weight of the mixture usually containing an acylglycerol, or a mixture of acylglycerols, with glycerol and fatty acids derived from said acylglycerol(s), such as Peceol® described above.

Acylglycerols are natural compounds, and may be extracted and/or derived from renewable vegetable sources. Their use is thus favored in terms of biocompatibility and environmental concerns when compared to synthetic compounds.

Sterol

The homogenous oil-based phase or reverse micellar system according to the invention comprises at least one sterol, preferably natural sterol, such as cholesterol or phytosterol (vegetable sterols). Sitosterol and cholesterol are the preferred sterols that can be present in a reverse micellar system according to the invention. Preferably, the reverse micellar system comprises sitosterol, such beta-sitosterol.

Sitosterol and cholesterol are commercially available. More particularly, commercial sitosterol, which is extracted from soya, can be used. In such a product, the sitosterol generally represents from 50 to 80% by weight of the product and is generally found in a mixture with campesterol and sitostanol in respective proportions in the order of 15% each. Commercial sitosterol, which is extracted from a variety of pine called tall oil, can also be used.

Lecithin

In the present invention, the term lecithin refers to phosphatidylcholine. Phosphatidylcholine is also known as 1,2-diacyl-glycero-3-phosphocholine or PtdCho. It is composed of a choline, a phosphate group, a glycerol and two fatty acids. It is actually a group of molecules, wherein the fatty acid compositions varies from one molecule to another. Phosphatidylcholine may be obtained from commercial lecithin that contains phosphatidylcholine in weight fractions from 20 to 98%. The lecithin preferably used according to the invention is Epikuron 200® (sold by Cargill Company) and contains phosphatidylcholine at a fraction of more than 90%. Preferably, the lecithin used according to the invention comprises more than 92% weight phosphatidylcholine.

Water

The water useful for the preparation of the reverse micellar system or homogenous oil-based phase according to the invention is preferably purified water; more particularly distilled or deionized water.

Ethanol

Ethanol is generally an ethanol-water solution, wherein the ethanol amount is from about 90% to 99% by volume. In a more particular embodiment, ethanol is absolute or anhydrous alcohol (that refers to ethanol with low water content). There are various grades with maximum water contents ranging from 1% to a few parts per million (ppm) levels. Absolute ethanol is preferred.

Other Components

The homogenous oil-based phase or reverse micellar system according to the invention may comprise any type of additional components. As example of additional component, one can cite alcohols different from ethanol.

The homogenous oil-based phase or reverse micellar system according to the invention may comprise at least one alcohol in addition to ethanol as defined above. The alcohols that may be used according to the invention are preferably linear or branched mono-alcohols with two to four carbons atoms. Examples of alcohols are 1-propanol, 2-propanol, 2-methyl-1-propanol, isopropanol, and any mixture thereof. Polyols that may be used according to the invention are preferably glycerol and propylene glycol.

The amounts of the components of the homogenous oil-based phase or reverse micellar system can be adapted by anyone of ordinary skill in the art depending on the desired properties for the phase or system, such as visual appearance, viscosity, and/or concentration of active agent for instance.

In a preferred embodiment, the homogenous oil-based phase or reverse-micellar system does not comprise liposomes.

In an embodiment of the invention, the amounts of the components of the homogenous oil-based phases or reverse micellar system are adjusted so that the reverse-micellar systems (i) or (ii) are in the form of a liquid. One of ordinary skill in the art can adapt the relative amounts of acylglycerol, sterol, lecithin, ethanol and water in the homogenous oil-based phases or reverse micellar systems for obtaining a liquid with the desired properties, such as the visual appearance, the viscosity, and/or the concentration of the active agent for instance.

Examples of amounts for different components of the biocompatible reverse micellar system comprising cyano-bridged coordination polymers obtained according to the invention are the following:

The reverse micellar system may comprise from 1 to 30%, preferably from 1 to 20%, in particular from 5 to 15% lecithin.

The reverse micellar system may comprise from 0.1 to 20%, preferably from 1 to 20%, in particular from 5 to 15% water.

The reverse micellar system may comprise from 5 to 20%, preferably from 5 to 15% alcohols, including ethanol.

The reverse micellar system may comprise from 0.82 to 4.5% sterol.

The reverse micellar system may comprise from 30 to 90%, preferably from 50 to 90% acylglycerol. Moreover, the amount of the obtained cyano-bridged coordination polymers is more particularly from 0.4-10%, preferably 0.5-5%, more preferably 1-2%, by weight of the total amount of water and cyano-bridged coordination polymers within the system.

The amounts of components in the biocompatible reverse micellar systems comprising the precursors, and therefore the homogenous oil-based phases and the aqueous solutions containing the metal precursors, are adapted by one skilled in the art as to obtain the preferred amounts as indicated above.

Unless otherwise specified, the percentage values used in the present invention are weight percentages with respect to the total weight of the named compounds or reverse micellar system.

In the present invention, the term "reverse micellar system" relates to a reverse-phase system comprising an aqueous phase dispersed in an oil phase. Preferably, the reverse-phase system comprises reverse or reverse swollen micelles, but these may be organized in higher ordered isotropic structures such as water-in-oil microemulsion or anisotropic structures such as cubic, hexagonal, lamellar organizations.

Cyano-Bridged Metal Nanoparticles

According to the method of the invention as described above, the cyano-bridged metal nanoparticles are thus obtained.

Another embodiment of the invention concerns a biocompatible reverse micellar system comprising at least one acylglycerol, a sterol, lecithin, ethanol, cyano-bridged metal nanoparticles, water, said biocompatible reverse micellar system does not comprise stabilizing agent. More particularly, the biocompatible reverse micellar system is obtainable by the method detailed herein.

As mentioned above, the amounts of the different components of the biocompatible reverse micellar system comprising cyano-bridged coordination polymers, more specifically obtained according to the invention, are the following:

The reverse micellar system may comprise from 1 to 30%, preferably from 1 to 20%, in particular from 5 to 15% lecithin.

The reverse micellar system may comprise from 0.1 to 20%, preferably from 1 to 20%, in particular from 5 to 15% water.

The reverse micellar system may comprise from 5 to 20%, preferably from 5 to 15% alcohols, including ethanol.

The reverse micellar system may comprise from 0.82 to 4.5% sterol.

The reverse micellar system may comprise from 30 to 90%, preferably from 50 to 90% acylglycerol. Moreover, the amount of the obtained cyano-bridged coordination polymers is more particularly from 0.4-10%, preferably 0.5-5%, more preferably 1-2%, by weight of the total amount of water and cyano-bridged coordination polymers within the system.

According to another embodiment, the invention relates to a composition comprising a biocompatible reverse micellar system of the invention. The composition is more particularly for use in therapy or diagnosis, as detailed below. According to a particular embodiment, the invention deals with a pharmaceutical composition comprising a biocompatible reverse micellar system of the invention in a pharmaceutically acceptable carrier or support.

More specifically, the cyano-bridged metal nanoparticles comprised in the biocompatible reverse micellar system according to the invention are advantageously stabilized by the reverse micellar system. The cyano-bridged metal nanoparticles comprised therein thus do not require a specific stabilizing agent.

The term "stabilizing agent" refers to any compound able to stabilize the nanoparticles, more specifically their size. Generally, the stabilizing agent are polyethyleneglycols (PEG) or derivatives thereof, such as PEG-amine, or polysaccharides, such as dextrans.

In the present invention, the term "cyano-bridged metal nanoparticles" refers to compounds in the form of nanoparticles (size of nanoparticles preferably ranges from 1 to 100 nm) comprising metallic cation $M^{p+}$ and cyano-metalate anions $[M'(CN)_n]^{q-}$, as defined above.

More specifically, the cyano-bridged metal nanoparticles comprise M'-CN-M bonds, such as Fe(II)-CN—Fe(III), Fe(II)-CN—Zn(II), Fe(II)-CN—Mn(II), Fe(II)-CN—[Fe(III)Mn(II)] or Fe(II)-CN—[Mn(II)Zn(II)].

The number of CN groups can range from 4 to 8, depending on the transition metal cation used. For instance, the number of CN groups is 4 with nickel, 6 with iron and 8 with molybdenum.

The term "cyano-bridged metal nanoparticles" also includes PB and any PBA.

The term "nanoparticles" according to the invention refers more specifically to particles where size ranges from 0.5 to 20 nm, preferably from 1 to 10 nm, more preferably from 1 to 5 nm. For instance, PB nanoparticles in reverse micellar systems prepared according to the invention (see sample A of examples) are discernable by Transmission Electron Microscopy (refers as TEM) images, which allows to state that PB nanoparticles according to the invention are more specifically with a diameter ranging from 1 to 5 nm.

Applications

The cyano-bridged coordination polymers possess intrinsic vacancies which can allow sorption of ionic compounds. Depending on the nature of these ionic compounds, the applications are quite large.

One of the objects of the invention is the sequestration of radionuclides cations within cyano-bridged metal nanoparticles in organic tissues, which is called decorporation.

In particular, the cesium decorporation can be considered. Many cyano-bridged metal nanoparticles can be used to decorporate with different efficiencies (Vincent, 2014). The traditional cyano-bridged metal nanoparticles are PB, known to efficiently decorporate cesium (McCargar, 1988 and Henge, 2000). The PB is not absorbed by oral route, the so-called Radiogardase® is a commercial drug available for cesium decorporation. However, as mentioned before, PB particles remain in the gastro intestinal tract, waiting to bind cesium atoms which are following the potassium path. PB nanoparticles within a reverse micellar system according to the invention could greatly enhance, in particular via an oral administration, the sorption of cesium with fewer amounts of doses and could therefore prevent unwanted side effects.

Accordingly, an object of the invention is a biocompatible reverse micellar system comprising cyano-bridged metal nanoparticles according to the present invention, wherein the biocompatible reverse micellar system or the cyano-bridged metal nanoparticles comprised therein are used for being substituted by and/or sequestering radionuclide and/or metal cation.

The terms "radionuclides cations" and "metal cations" refer in the present invention to any chemical form of said radionuclides and metal cations. For instance, the radionuclides and/or metal cations that are substitutes and/or are sequestered according to the present invention may be in ionic form, optionally with at least one counter-anion or complexed with at least one other ligand, solvated or in the form of an oxide, before substitution or sequestration.

According to the present invention, "substitution" and derivatives of this term relate to the exchange of one or more atom(s) from the cyano-bridged metal nanoparticles with one or more radionuclide(s) and/or metal cation(s) in the medium. More specifically, the term "substitution" is used for Gadolinium and Manganese cations.

According to the invention, "sequestration" and derivatives of this term relate to the capture of one or more atom(s) by one or more cyano-bridged metal nanoparticles vacancy(ies) in the medium. More specifically, the term "sequestration" is used for Cesium and Thallium cations.

For instance, the biocompatible reverse micellar system of the invention or the cyano-bridged metal nanoparticles comprised therein can be used for being substituted by a metal cation, which favors thereby excretion of the metal cation comprised in the patient's body. Said metal cation may come for instance from an external intoxication (exposure to a metal cation) or to a pathology triggering cation accumulation in the patient's body.

The term "decorporation" is used in the present invention in relation with a radionuclide cation to refer to the elimination of at least some of said radionuclide cation from the patient body.

In an embodiment, the biocompatible reverse micellar system of the invention or the cyano-bridged metal nanoparticles comprised therein according to the invention or a composition comprising the same is used for decorporating at least one radionuclide cation and/or treating at least one metal cation intoxication from the patient body. In this embodiment, decorporation or treatment of intoxication comprises the substitution by and/or sequestering of the metal and/or radionuclide cation with the biocompatible reverse micellar system of the invention or the cyano-bridged metal nanoparticles comprised therein and the elimination and/or excretion of the substitute and/or sequestered metal or radionuclide cation from the patient's body. In a preferred embodiment, the excretion is through natural routes, such as by urine or feces.

In the present invention, the terms treatment or decorporation refer to any preventive and/or curative action that is capable of suppressing or decreasing the duration or intensity of any symptom due to the exposure to the radionuclide and/or metal cation, or improving in any manner the state of health or comfort of the patient.

In an embodiment, the metal or radionuclide cation is toxic for the patient, or the amount of said metal or radionuclide cation present in the patient is toxic.

The term "radionuclide cation", or radioactive nuclide cation, refers to a cation atom with an unstable nucleus, characterized by excess energy available to be imparted either to a newly created radiation particle within the nucleus or via internal conversion. During this process, the radionuclide cation is said to undergo radioactive decay, resulting in the emission of gamma ray(s) and/or subatomic particles such as alpha or beta particles.

Depending on the nature of the cyano-bridged metal nanoparticles comprised in the reverse-micellar system, said system is appropriate for decorporation of any type of radionuclide cation. When the radionuclide cation is a specific isotope of an element, the reverse-micellar system will not necessarily more selectively be substituted by the radioactive isotope than the other isotopes of the same element.

In embodiments, the radionuclide cation is selected from the group consisting of plutonium, for instance $^{238}$Pu, $^{239}$Pu or $^{240}$Pu, americium, for instance $^{241}$Am, uranium, for instance $^{233}$U, $^{234}$U, $^{235}$U, or $^{238}$U, cesium, for instance $^{134}$Cs, $^{135}$Cs or $^{137}$Cs, thallium, for instance $^{201}$Tl or $^{204}$Tl, indium, for instance $^{111}$In, strontium, for instance $^{85}$Sr, $^{89}$Sr or $^{90}$Sr, molybdenum, for instance $^{99}$Mo or $^{100}$Mo, lead, for instance $^{210}$Pb, chromium, for instance $^{51}$Cr, polonium, for instance $^{210}$Po, cobalt, for instance $^{57}$Co, $^{58}$Co or $^{60}$Co, copper, for instance $^{64}$Cu or $^{67}$Cu, gallium, for instance $^{67}$Ga, technetium, for instance $^{99m}$Tc, and degradation products thereof. The radionuclide cation is more preferably cesium, thallium or some lanthanides cations.

The selectivity of the reverse-micellar system according to the invention for being substituted by or sequestering the radionuclides and/or metals cations is linked to the selectivity of the metals cations within the cyano-bridged metal nanoparticles.

Accordingly, the cyano-bridged metal nanoparticles are preferably selective of two main atoms such as cesium ($^{135}$Cs or $^{137}$Cs) and thallium ($^{201}$Tl or $^{204}$Tl).

By way of example, PB is known to be appropriate for sequestering cesium and/or thallium. Accordingly, when the cyano-bridged metal nanoparticles comprised in the biocompatible reverse micellar system of the invention are PB nanoparticles, the biocompatible reverse micellar system of the invention or the PB nanoparticles comprised therein is used for capturing at least one cesium or thallium.

The metal cation that can be the substitute of and/or sequestered by the cyano-bridged metal nanoparticles according to the invention may be any metal cation. For instance, the metal cation can be a transition metal cation, a heavy metal cation, a lanthanide cation or an alkali metal cation.

In an embodiment, the metal cation that can be the substitute of and/or sequestered is selected from iron, aluminum, mercury, lead, arsenic, cadmium, cesium, copper, gold, beryllium, bismuth, cobalt, chromium, nickel, protactinium, polonium, silver, platinum, antimony, selenium, tin, technetium, titanium, zinc, manganese, and thallium. In a particular embodiment, the metal cation is cesium.

In an embodiment, the biocompatible reverse micellar system of the invention or the cyano-bridged metal nanoparticles comprised therein or a composition comprising the same is used in the reduction of the cumulative radiation dose delivered to the tissues by internalized radionuclides cations. Indeed, the only possibility is decorporation of radionuclides cations by sequestration, as to facilitate their excretion by natural means, such as urines or feces. According to a specific embodiment, the biocompatible reverse micellar system of the invention or the cyano-bridged metal nanoparticles comprised therein or a composition comprising the same is for use in the reduction of the risk of developing diseases due to the cumulative radiation dose delivered to the tissues by radionuclides cations.

According to a specific embodiment, the biocompatible reverse micellar system of the invention or the cyano-bridged metal nanoparticles comprised therein or a composition comprising the same is for use in the treatment of at least one disease linked to the accumulation and/or overload of at least one radionuclide cation in a patient in need thereof.

The diseases (or pathologies) linked to the accumulation and/or overload of at least one radionuclide cation may vary depending on the radiation exposure (duration and/or amount), it can include gastrointestinal disorders, such as nausea or vomiting, symptoms related to falling blood counts, such as predisposition to infection or bleeding, neurological disorders, or different types of cancers (such as blood cancers or thyroid cancer).

Exposure to radionuclides cations and thus accumulation and/or overload of radionuclides cations may have different origins, from the involvement of a nuclear worker after breaking of the containment of a glove box for example, to that of a multitude of people contaminated by the widespread dissemination of radionuclides cations in the environment, such as: incident/accident or natural disaster affecting facilities of research, production, operation or storage of nuclear materials, military conflict with nuclear weapons, radionuclide cation containing weapons, terrorist act aiming at these facilities or characterized by an explosive device dispersing radionuclides cations called "dirty bomb."

Internalized radionuclides cations are highly toxic and may cause both acute and chronic radiation injuries. The most frequently encountered nuclides in these scenarios include actinides cations, such as americium, plutonium or uranium and transition metal cations, such as cesium or strontium. Once internalized in the body, the nuclide is distributed in various tissues and/or organs (e.g. the lungs, muscles, bone and/or liver).

In a particular embodiment, the cyano-bridged metal nanoparticles comprised in the biocompatible reverse micellar system of the invention are PB nanoparticles. The biocompatible reverse micellar system of the invention or the PB nanoparticles comprised therein or the composition comprising the same is used for decorporating at least one cesium or thallium or for the treatment of at least one disease linked to the accumulation and/or overload of cesium or thallium in a patient in need thereof.

The patient to be treated can be any mammal, non-human or human mammals, and more specifically children.

Another object of the invention is the biocompatible reverse micellar system of the invention or the cyano-bridged metal nanoparticles comprised therein or a composition comprising the same are used as a contrast agent and/or as a diagnosis agent.

Cyano-bridged metal nanoparticles are well known as contrast agent for Magnetic Resonance Imaging (MRI) and imaging agent for Scintigraphy. With a transmucosal delivery, the absorption and/or the quality of cyano-bridged metal nanoparticles within the body can be increased which may improve the quality of the images obtained by the imaging techniques. In particular, Manganese-based contrast agent (Pan, 2011, Massaad, 2011 and Zhu, 2015) and Gadolinium-based contrast agent (Mohs, 2007 and Zhou, 2013) were investigated for MRI uses. However, both types are quite toxic at a certain level of dose and the administered quantities must be decreased. So, the use of cyano-bridged metal nanoparticles containing $Mn^{2+}$ and $Gd^{3+}$ ions within a reverse micellar system should:

(i) improve the longitudinal relaxivity values permitting the administration of the contrast agent in lower doses, and/or (ii) improve the pharmacokinetics by increasing the body circulation time, and/or (iii) decrease the toxicity.

Furthermore, the advantage to use a transmucosal system lies in the breach of the blood-brain barrier. More particularly, the cyano-bridged metal nanoparticles within the reverse micellar system can actually allow imaging of the brain.

Depending on the nature of the metal cation involved in the cyano-bridged metal network, compounds presenting magnetic properties interesting for imaging methods (such as MRI) can be formed within the reverse micellar system.

According to a particular embodiment, the cyano-bridged metal nanoparticles comprised in the reverse micelle system of the invention are gadolinium- or manganese-substituted (containing) PB nanoparticles, and can preferably be used as contrast agent and/or as a diagnosis agent.

The contrast agent can be a magnetic contrast agent (such as for MRI), an imaging agent for Scintigraphy, a spectroscopic contrast agent, or a microscopic contrast agent. In that respect, the contrast agent can be used as a diagnosis tool or agent.

Another object of the invention is a method of imaging at least part of at least one organ of a patient, comprising the administration of the biocompatible reverse micellar system of the invention or the cyano-bridged metal nanoparticles comprised therein or a composition comprising the same. Said method of imaging advantageously further comprises a step of detecting the emitted radiation and/or signal, and preferably a step of forming an image therefrom.

Another object of the invention is the use of the biocompatible reverse micellar system of the invention or the cyano-bridged metal nanoparticles comprised therein or a composition comprising the same, in the preparation of a composition to be used in a method of imaging and/or diagnosis.

The amount of reverse-micellar system to be administered for implementing the imaging method can be easily adapted by anyone of ordinary skill in the art in function of the amount of cyano-bridged metal nanoparticles, the area(s) to visualize with this imaging method, and the imaging technique used.

The method of imaging may be for instance scintigraphy or MRI. In an embodiment, the method of imaging is scintigraphy of bone, kidney, liver, brain and/or lung. The term "contrast agent" refers in the present invention to an agent that can be advantageously used in a method of imaging to improve the quantity and/or quality of the emitted radiation and/or signal or of the image formed therefrom.

Another object of the invention is thus a reverse-micellar system for use as contrast agent according to the invention, wherein the contrast agent is used in scintigraphy and/or MRI.

The contrast agent may also be used for studying the perfusion of the renal and/or urinary tract function, or for determining the glomerular filtration rate.

The method of imaging according to the invention may be part of a diagnosis method for determining pathology, preferably pathology of the visualized area, for instance bone, kidney, brain and/or lung pathology. The term "diagnosis agent" refers in the present invention to an agent that can be advantageously used to help determining the existence of a pathology or of a risk of pathology, for instance a pathology of the bones, kidneys, brain and/or lungs.

Administration of the Reverse-Micellar Systems

The reverse micellar-systems according to the invention are able to be absorbed through mucosa and to vectorize cyano-bridged metal nanoparticles under a protected form to any tissue and/or organs of the organism.

The reverse-micellar system may be administered via different routes. In a preferred embodiment of the invention, the reverse-micellar system is administered by topical, oral, or transmucosal route.

As used herein, the terms "mucosa" and "mucosal" refer to a mucous tissue such as of the respiratory, digestive, or genital tissue. "Transmucosal delivery", "mucosal delivery", "mucosal administration" and analogous terms as used herein refer to the administration of a composition through a mucosal tissue. "Transmucosal delivery", "mucosal delivery", "mucosal administration" and analogous terms include, but are not limited to, the delivery of a composition through bronchi, gingival, lingual, nasal, oral, buccal, oesophageal, vaginal, rectal, and gastro-intestinal mucosal tissue.

In a specific embodiment, the mucosal administration is through buccal mucosal tissue.

According to another embodiment, the reverse-micellar system of the invention can be orally administered to be active at the gastrointestinal tract. This is more specifically suitable for PB particles of the invention.

The reverse-micellar system can be administered according to the invention at any time with respect to the exposure to and/or contamination with metal and/or radionuclide cation(s).

In an embodiment, the reverse-micellar system is administered preventively, that means before the exposure to and/or contamination with the radionuclide and/or metal cation(s).

In another embodiment, the reverse-micellar system is administered in the first day, preferably in the first hours, in particular in the first 20 minutes, following the exposure to and/or contamination with the radionuclide and/or metal cation(s).

In another embodiment, the reverse-micellar system is administered more than 24 hours, preferably more than 48 hours, in particular more than 96 hours, after the end of the exposure to the radionuclide and/or metal cation(s).

The reverse-micellar system of the invention can be effective for decorporating a radionuclide cation when the treatment is started immediately after 1 hour, 4 days after, and even 7 days after the contamination, preferably the internal contamination.

The skilled practitioner will be able to adapt the number of daily administrations, the amount to be administered, the frequency of administration and/or the moment when the treatment is started in function of the amount of active agent present in the reverse-micellar system and the type and intensity of the contamination with the metal or radionuclide cation.

In the embodiment where the biocompatible reverse-micellar system is used in the treatment of a pathology linked to the accumulation of at least one metal cation in a patient in need thereof, the pathology is not necessarily initiated by exposure to said metal cation. The pathology may also be linked to chronic exposure to a metallic cation.

The biocompatible reverse-micellar system may be formulated in a composition that may further comprise a pharmaceutically acceptable support.

Another object of the invention is a pharmaceutical composition comprising a pharmaceutically acceptable support or carrier and a biocompatible reverse-micellar system of the invention.

The term "pharmaceutically acceptable support or carrier" refers to any pharmaceutically acceptable excipient, vehicle or carrier, well-known to the person skilled in the art. Other additives well-known to the person skilled in the art such as stabilisers, drying agents, binders or pH buffers may also be used. Preferred excipients in accordance with the invention promote adherence of the finished product to the mucosa.

According to particular embodiments, the pharmaceutical composition is in the form of a capsule, a caplet, an aerosol, a spray, a solution, a soft elastic gelatin capsule or syrup According to the invention, the term "comprise(s)" or "comprising" can be generally interpreted such that all of the specifically mentioned features and any optional, additional and unspecified features are included; it can also be interpreted more specifically as the expression "consisting of" where only the specified features are included, unless otherwise specified.

The present invention includes the specific embodiments as described above and any combination thereof.

In the present invention, the percentage values are weight percentage values, unless otherwise indicated.

The term "around" or "about" a value refers to a range between ±10% of the value.

The following examples are provided only as illustrative, and not limitative, of the invention.

EXAMPLES

Example 1: Nanoparticles of Transition Metal Hexacyanometalate are In Situ Prepared and Stabilized in a Reverse Micellar System Preparation of Sample A A1: 0.11 g of commercially available ferric chloride hexahydrate, with purity above 97%, was dissolved in 9.89 g of water for HPLC at room temperature after 10 seconds of vortex.

A2: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase (or homogenous oil-based phase).

A3: 1.20 g of A1 was added to 8.80 g of A2 at room temperature and the mixture was vortexed for 10 seconds to achieve an isotropic and homogenous reverse micellar phase containing the first precursor of PB.

A4: 0.15 g of commercially available sodium hexacyanoferrate(II) decahydrate, with purity above 99%, was dissolved in 9.85 g of water for HPLC at room temperature after 10 seconds of vortex.

A5: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

A6: 1.20 g of A4 was added to 8.80 g of A5 at room temperature and the mixture was vortexed for 10 seconds to achieve an isotropic and homogenous reverse micellar phase containing the second precursor of PB.

A: 2.00 g of A3 and 2.00 g of A6 were together vortexed for 10 seconds at room temperature to obtain spontaneously in situ nanoparticles formation of PB.

Another reverse micellar system without any active compound or precursor was prepared as follows: 1.20 g of water for HPLC was added to 8.80 g of A2 at room temperature and the mixture was vortexed for 10 seconds to achieve an isotropic and homogenous reverse micellar system (sample A7).

Preparation of Sample B

B1: 0.04 g of commercially available zinc chloride tetrahydrate, with purity above 98%, was dissolved in 9.96 g of water for HPLC at room temperature after 10 seconds of vortex.

B2: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

B3: 1.20 g of B1 was added to 8.80 g of B2 at room temperature and the mixture was vortexed for 10 seconds to achieve an isotropic and homogenous reverse micellar phase containing the first precursor of the PBA.

B4: 0.07 g of commercially available potassium hexacyanoferrate(III), with purity above 99%, was dissolved in 9.93 g of water for HPLC at room temperature after 10 seconds of vortex.

B5: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

B6: 1.20 g of B4 was added to 8.80 g of B5 at room temperature and the mixture was vortexed for 10 seconds to achieve an isotropic and homogenous reverse micellar phase containing the second precursor of the PBA.

B: 2.00 g of B3 and 2.00 g of B6 were together vortexed for 10 seconds at room temperature to obtain spontaneously in situ nanoparticles formation of PBA.

Preparation of Sample C

C1: 0.06 g of commercially available manganese chloride tetrahydrate, with purity above 99%, was dissolved in 9.94 g of water for HPLC at room temperature after 10 seconds of vortex.

C2: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

C3: 1.20 g of C1 was added to 8.80 g of C2 at room temperature and the mixture was vortexed for 10 seconds to achieve an isotropic and homogenous reverse micellar phase containing the first precursor of PBA.

C4: 0.07 g of commercially available potassium hexacyanoferrate(III), with purity above 99%, was dissolved in 9.93 g of water for HPLC at room temperature after 10 seconds of vortex.

C5: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

C6: 1.20 g of C4 was added to 8.80 g of C5 at room temperature and the mixture was vortexed for 10 seconds to achieve an isotropic and homogenous reverse micellar phase containing the second precursor of PBA.

C: 2.00 g of C3 and 2.00 g of C6 were together vortexed for 10 seconds at room temperature to obtain spontaneously in situ nanoparticles formation of PBA.

Preparation of Sample D (5%)

D1: 0.008 g of commercially available manganese chloride tetrahydrate, with purity above 99%, and 0.199 g of commercially available ferric chloride hexahydrate, with purity above 97%, were dissolved in 9.793 g of water for HPLC at room temperature after 10 seconds of vortex.

D2: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

D3: 1.20 g of D1 was added to 8.80 g of D2 at room temperature and the mixture was vortexed for 10 seconds to achieve an isotropic and homogenous reverse micellar phase containing the first precursor of PBA.

D4: 0.317 g of commercially available sodium hexacyanoferrate(II) decahydrate, with purity above 99%, was dissolved in 9.683 g of water for HPLC at room temperature after 10 seconds of vortex.

D5: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

D6: 1.20 g of D4 was added to 8.80 g of D5 at room temperature and the mixture was vortexed for 10 seconds to achieve an isotropic and homogenous reverse micellar phase containing the second precursor of PBA.

D (5%): 4.00 g of D3 and 4.00 g of D6 were together vortexed for 10 seconds at room temperature to obtain spontaneously in situ nanoparticles formation of PBA.

Preparation of Sample D (10%)

D1: 0.016 g of commercially available manganese chloride tetrahydrate, with purity above 99%, and 0.188 g of commercially available ferric chloride hexahydrate, with purity above 97%, were dissolved in 9.796 g of water for HPLC at room temperature after 10 seconds of vortex.

D2: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

D3: 1.20 g of D1 was added to 8.80 g of D2 at room temperature and the mixture was vortexed for 10 seconds to achieve an isotropic and homogenous reverse micellar phase containing the first precursor of PBA.

D4: 0.317 g of commercially available sodium hexacyanoferrate(II) decahydrate, with purity above 99%, was dissolved in 9.683 g of water for HPLC at room temperature after 10 seconds of vortex.

D5: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

D6: 1.20 g of D4 was added to 8.80 g of D5 at room temperature and the mixture was vortexed for 10 seconds to achieve an isotropic and homogenous reverse micellar phase containing the second precursor of PBA.

D (10%): 4.00 g of D3 and 4.00 g of D6 were together vortexed for 10 seconds at room temperature to obtain spontaneously in situ nanoparticles formation of PBA.

Preparation of Sample D (25%)

D1: 0.040 g of commercially available manganese chloride tetrahydrate, with purity above 99%, and 0.157 g of commercially available ferric chloride hexahydrate, with purity above 97%, were dissolved in 9.803 g of water for HPLC at room temperature after 10 seconds of vortex.

D2: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

D3: 1.20 g of D1 was added to 8.80 g of D2 at room temperature and the mixture was vortexed for 10 seconds to achieve an isotropic and homogenous reverse micellar phase containing the first precursor of PBA.

D4: 0.317 g of commercially available sodium hexacyanoferrate(II) decahydrate, with purity above 99%, was dissolved in 9.683 g of water for HPLC at room temperature after 10 seconds of vortex.

D5: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

D6: 1.20 g of D4 was added to 8.80 g of D5 at room temperature and the mixture was vortexed for 10 seconds to achieve an isotropic and homogenous reverse micellar phase containing the second precursor of PBA.

D (25%): 4.00 g of D3 and 4.00 g of D6 were together vortexed for 10 seconds at room temperature to obtain spontaneously in situ nanoparticles formation of PBA.

Preparation of Sample D (50%)

D1: 0.080 g of commercially available manganese chloride tetrahydrate, with purity above 99%, and 0.105 g of commercially available ferric chloride hexahydrate, with purity above 97%, were dissolved in 9.815 g of water for HPLC at room temperature after 10 seconds of vortex.

D2: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

D3: 1.20 g of D1 was added to 8.80 g of D2 at room temperature and the mixture was vortexed for 10 seconds to achieve an isotropic and homogenous reverse micellar phase containing the first precursor of PBA.

D4: 0.317 g of commercially available sodium hexacyanoferrate(II) decahydrate, with purity above 99%, was dissolved in 9.683 g of water for HPLC at room temperature after 10 seconds of vortex.

D5: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

D6: 1.20 g of D4 was added to 8.80 g of D5 at room temperature and the mixture was vortexed for 10 seconds to achieve an isotropic and homogenous reverse micellar phase containing the second precursor of PBA.

D (50%): 4.00 g of D3 and 4.00 g of D6 were together vortexed for 10 seconds at room temperature to obtain spontaneously in situ nanoparticles formation of PBA.

Preparation of Sample D (75%)

D1: 0.120 g of commercially available manganese chloride tetrahydrate, with purity above 99%, and 0.052 g of commercially available ferric chloride hexahydrate, with purity above 97%, were dissolved in 9.828 g of water for HPLC at room temperature after 10 seconds of vortex.

D2: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

D3: 1.20 g of D1 was added to 8.80 g of D2 at room temperature and the mixture was vortexed for 10 seconds to achieve an isotropic and homogenous reverse micellar phase containing the first precursor of PBA.

D4: 0.317 g of commercially available sodium hexacyanoferrate(II) decahydrate, with purity above 99%, was dissolved in 9.683 g of water for HPLC at room temperature after 10 seconds of vortex.

D5: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

D6: 1.20 g of D4 was added to 8.80 g of D5 at room temperature and the mixture was vortexed for 10 seconds to achieve an isotropic and homogenous reverse micellar phase containing the second precursor of PBA.

D (75%): 4.00 g of D3 and 4.00 g of D6 were together vortexed for 10 seconds at room temperature to obtain spontaneously in situ nanoparticles formation of PBA.

Preparation of Sample E

E1: 0.06 g of commercially available manganese chloride tetrahydrate, with purity above 99%, was dissolved in 9.94 g of water for HPLC at room temperature after 10 seconds of vortex.

E2: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

E3: 1.20 g of E1 was added to 8.80 g of E2 at room temperature and the mixture was vortexed for 10 seconds to achieve an isotropic and homogenous reverse micellar phase containing the first precursor of PBA.

E4: 0.04 g of commercially available zinc chloride tetrahydrate, with purity above 98%, was dissolved in 9.96 g of water for HPLC at room temperature after 10 seconds of vortex.

E5: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

E6: 1.20 g of E4 was added to 8.80 g of E5 at room temperature and the mixture was vortexed for 10 seconds to achieve an isotropic and homogenous reverse micellar phase containing the first precursor of the PBA.

E7: 0.07 g of commercially available potassium hexacyanoferrate(III), with purity above 99%, was dissolved in 9.93 g of water for HPLC at room temperature after 10 seconds of vortex.

E8: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

E9: 1.20 g of E7 was added to 8.8 g of E8 at room temperature and the mixture was vortexed for 10 seconds to achieve an isotropic and homogenous reverse micellar phase containing the second precursor of PBA.

E: 2.00 g of E3, 2.00 g of E6 and 4.00 g of E9 were together vortexed for 10 seconds at room temperature to obtain spontaneously in situ nanoparticles formation of PBA.

Example 2: Nanoparticles of Transition Metal Tetracyanometalate in a Reverse Micellar System Preparation of Sample F F1: 0.06 g of commercially available ferric chloride hexahydrate, with purity above 97%, is dissolved in 9.94 g of water for HPLC at room temperature after 10 seconds of vortex.

F2: 1.50 g of commercially available lecithin, containing more than 97% of phosphatidylcholine, is dissolved in 1.30 g of absolute ethanol under magnetic stirring at 300 r/min and room temperature. 0.25 g of beta-sitosterol is dissolved in the mixture in the same conditions. 5.75 g of Peceol® are added thereto and magnetic stirring is carried out at 700 r/min and 37° C. to form an oily homogenous phase.

F3: 1.20 g of F1 is added to 8.80 g of F2 at room temperature and the mixture is vortexed for 10 seconds to achieve an isotropic and homogenous reverse micellar phase containing the first precursor of PBA.

F4: 0.07 g of commercially available potassium tetracyanonickelate, with purity above 99%, is dissolved in 9.93 g of water for HPLC at room temperature after 10 seconds of vortex.

F5: 1.50 g of commercially available lecithin, containing more than 97% of phosphatidylcholine, is dissolved in 1.30 g of absolute ethanol under magnetic stirring at 300 r/min and room temperature. 0.25 g of beta-sitosterol is dissolved in the mixture in the same conditions. 5.75 g of Peceol® are added thereto and magnetic stirring is carried out at 700 r/min and 37° C. to form an oily homogenous phase.

F6: 1.20 g of F4 was added to 8.80 g of F5 at room temperature and the mixture is vortexed for 10 seconds to achieve an isotropic and homogenous reverse micellar phase containing the second precursor of PBA.

F: 2.00 g of F3 and 2.00 g of F6 are together vortexed for 10 seconds at room temperature to obtain spontaneously in situ nanoparticles formation of PBA.

Example 3: Nanoparticles of Transition Metal Octacyanometalate in a Reverse Micellar System Preparation of Sample G G1: 0.11 g of commercially available ferric chloride hexahydrate, with purity above 97%, is dissolved in 9.89 g of water for HPLC at room temperature after 10 seconds of vortex.

G2: 1.50 g of commercially available lecithin, containing more than 97% of phosphatidylcholine, is dissolved in 1.30 g of absolute ethanol under magnetic stirring at 300 r/min and room temperature. 0.25 g of beta-sitosterol is dissolved in the mixture in the same conditions. 5.75 g of Peceol® are added thereto and magnetic stirring is carried out at 700 r/min and 37° C. to form an oily homogenous phase.

G3: 1.20 g of G1 is added to 8.80 g of G2 at room temperature and the mixture is vortexed for 10 seconds to achieve an isotropic and homogenous reverse micellar phase containing the first precursor of PBA.

G4: 0.09 g of molybdenum or tungsten octacyanide is dissolved in 9.91 g of water for HPLC at room temperature after 10 seconds of vortex.

G5: 1.50 g of commercially available lecithin, containing more than 97% of phosphatidylcholine, is dissolved in 1.30 g of absolute ethanol under magnetic stirring at 300 r/min and room temperature. 0.25 g of beta-sitosterol is dissolved in the mixture in the same conditions. 5.75 g of Peceol® are added thereto and magnetic stirring is carried out at 700 r/min and 37° C. to form an oily homogenous phase.

G6: 1.20 g of G4 is added to 8.80 g of G5 at room temperature and the mixture is vortexed for 10 seconds to achieve an isotropic and homogenous reverse micellar phase containing the second precursor of PBA.

G: 2.00 g of G3 and 2.00 g of G6 are together vortexed for 10 seconds at room temperature to obtain spontaneously in situ nanoparticles formation of PBA.

Example 4: Nanoparticles of Lanthanide Hexacyanometalate are In Situ Prepared and Stabilized in a Reverse Micellar System Preparation of Sample H H1: 0.09 g of commercially available gadolinium (III) nitrate hexahydrate, with purity above 99.9%, was dissolved in 9.91 g of water for HPLC at room temperature after 10 seconds of vortex.

H2: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

H3: 1.20 g of H1 was added to 8.80 g of H2 at room temperature and the mixture was vortexed for 10 seconds to achieve an isotropic and homogenous reverse micellar phase containing the first precursor of PBA.

H4: 0.07 g of commercially available potassium hexacyanoferrate, with purity above 99%, was dissolved in 9.93 g of water for HPLC at room temperature after 10 seconds of vortex.

H5: 1.50 g of commercially available lecithin, containing more than 97% of phosphatidylcholine, was dissolved in 1.30 g of absolute ethanol under magnetic stirring at 300 r/min and room temperature. 0.25 g of beta-sitosterol was dissolved in the mixture in the same conditions. 5.75 g of Peceol® were added thereto and magnetic stirring was carried out at 700 r/min and 37° C. to form an oily homogenous phase.

H6: 1.20 g of H4 was added to 8.80 g of H5 at room temperature and the mixture was vortexed for 10 seconds to achieve an isotropic and homogenous reverse micellar phase containing the second precursor of PBA.

H: 2.00 g of H3 and 2.00 g of H6 were together vortexed for 10 seconds at room temperature to obtain spontaneously in situ nanoparticles formation of PBA.

Example 5: Visual Observations of the In Situ Prepared and Stabilized Cyano-Bridged Metal Nanoparticles in the Reverse Micellar System After the in situ formation of the cyano-bridged metal nanoparticles, visual observations show that all the samples are stable, homogenous, and isotropic. A unique phase is observed and the turbidity is absent.

Example 6: FTIR Characterization of the In Situ Cyano-Bridged Metal Nanoparticles Formation in the Reverse Micellar System The samples A, B, C, D and E can be characterized by infrared measurements. This technique was used in order to analyze the stretching and binding vibrations of the M'-CN-M bonds that are the signatures of the nanoparticles formation. Particularly, the stretching vibrations of CN are evidenced in the 2000-2100 cm$^{-1}$ wavenumber region.

In the case of sample A, the Fe(II)-CN—Fe(III) bonds induce a single peak and the stretching mode is detected at 2086 cm$^{-1}$ as reported by Ghosh, 1974 and Ellis, 1981.

In the case of sample B, the Fe(III)-CN—Zn(II) bonds induce a single broad peak and the stretching mode is detected at 2092 cm$^{-1}$ as reported by Denisova, 2009 and Vincent, 2014.

In the case of sample C, the Fe(III)-CN—Mn(II) bonds induce a thin peak and the stretching mode is detected at 2071 cm$^{-1}$ as reported by Chugh, 2012.

Figure 2:
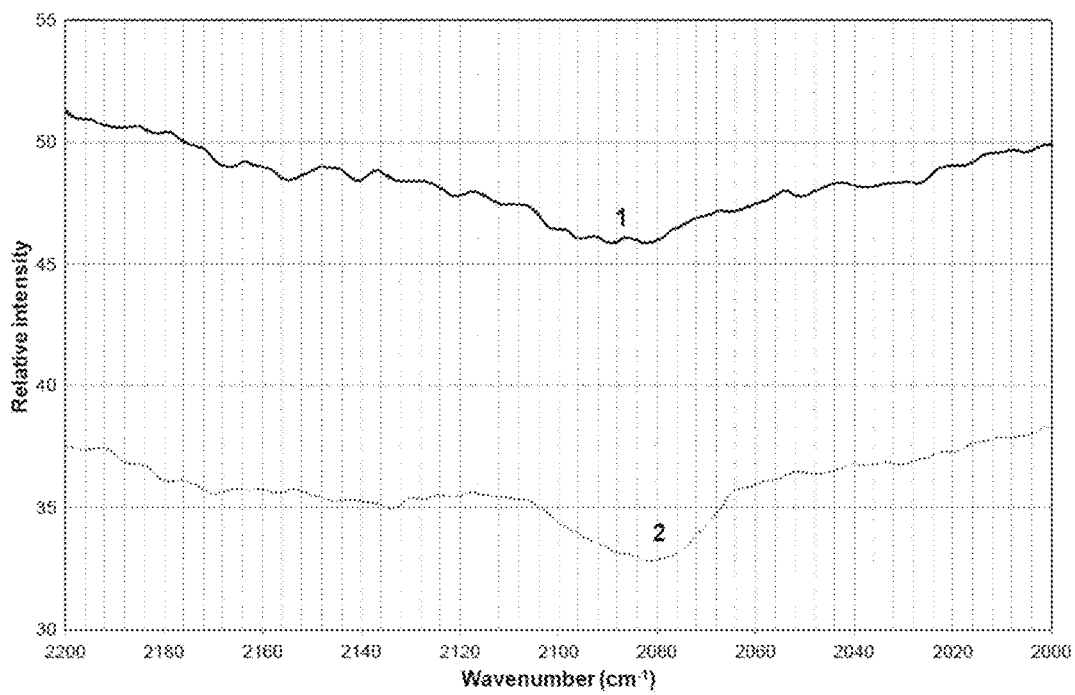
FIG. 2: FTIR (Fourier Transform InfraRed) spectra of (1) Fe(II)-CN—Fe(III) nanoparticles (Sample A) in the reverse micellar system and (2) the ferrocyanide precursor (Sample A6) in the reverse micellar system
Figure 3:
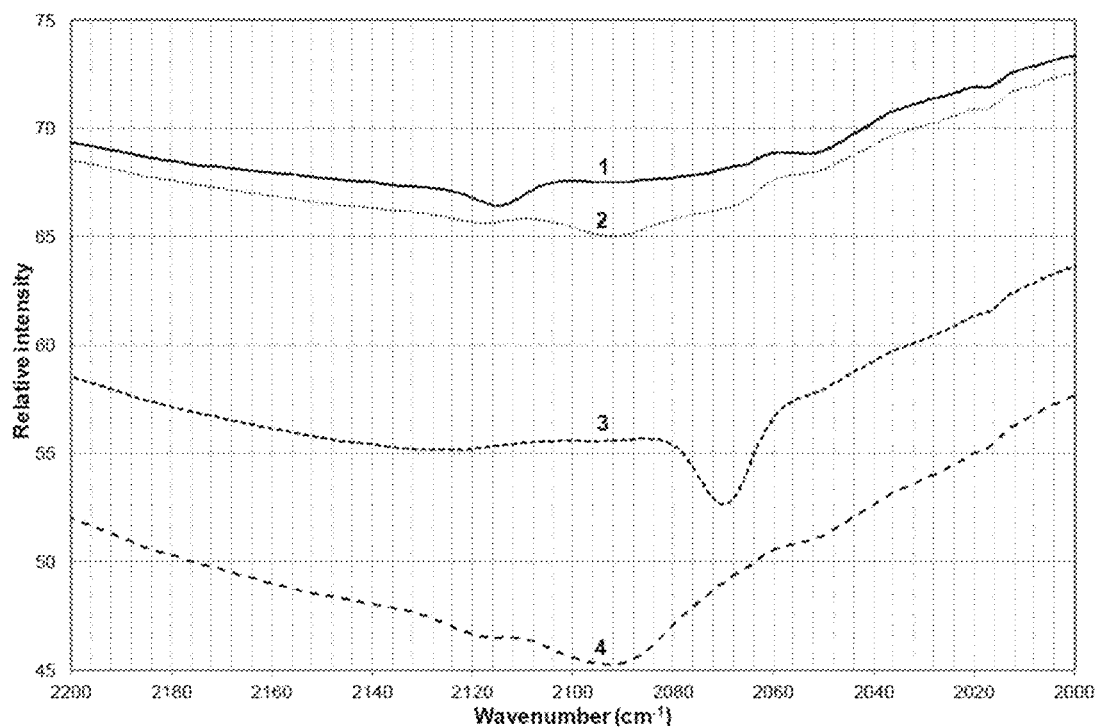
FIG. 3: FTIR spectra of (1) the ferrocyanide precursor (Sample A6), (2) the Fe(III)-CN—{Mn(II), Zn(II)} nanoparticles (Sample E), (3) the Fe(III)-CN—Mn(II) (Sample C) and (4) the Fe(III)-CN—Zn(II) (Sample B), all within the reverse micellar system

The FTIR spectra are showed in FIGS. 2 and 3.

Figure 4:
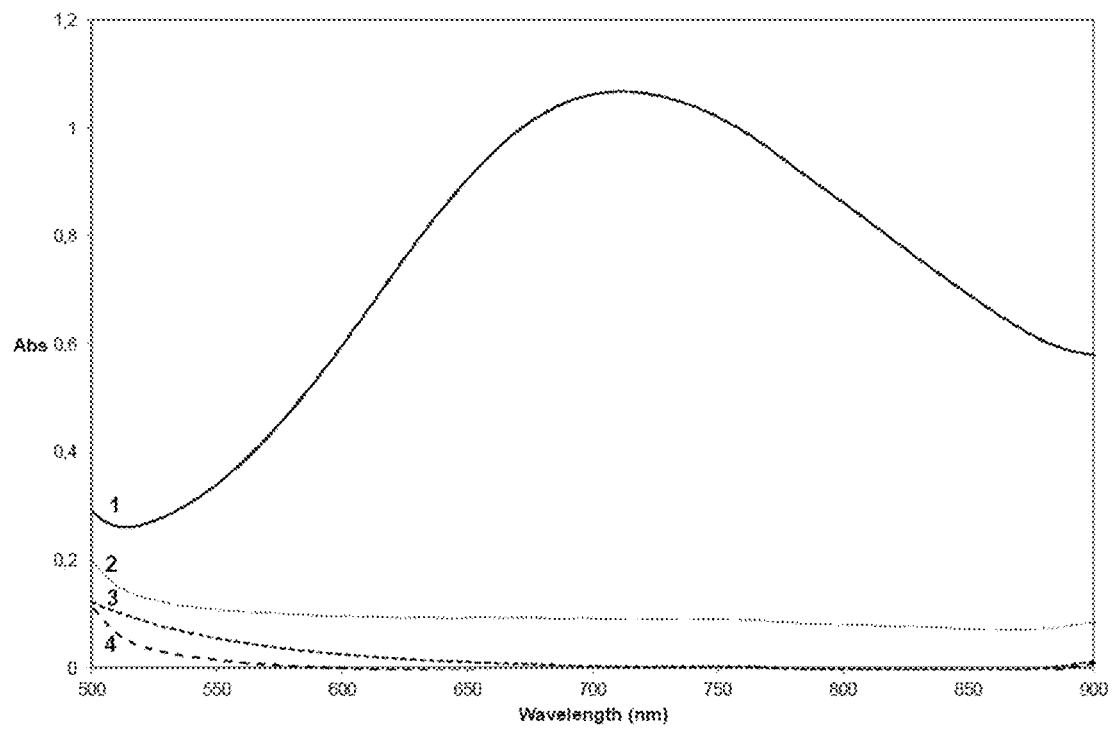
FIG. 4: UV-visible spectra of (1) the PB nanoparticles (Sample A), (2) the ferrocyanide precursor (Sample A6), (3) the iron chloride precursor (Sample A3), all within the reverse micellar system and (4) Sample A7

Example 7: UV-Visible Characterization of In Situ Prepared and Stabilized PB Nanoparticles in the Reverse Micellar System Sample A is the only sample which can be characterized by the UV-visible technique. Indeed, the PB cyano-bridged metal nanoparticles absorbs in the visible domain. This is due to the inter-metal charge transfer between $Fe^{2+}$ and $Fe^{3+}$ through the CN bond at a wavelength of 685 to 695 nm (Riter, 1998, Uemura, 2004). The absorbance spectra are showed in FIG. 4.

Figure 5:
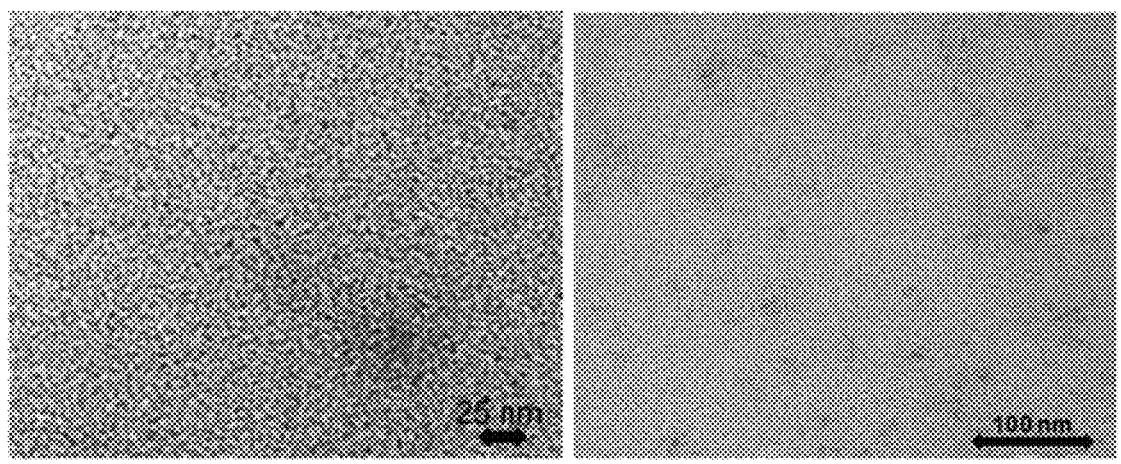
FIG. 5: TEM (Transmission Electron Microscopy) images of Sample A comprising PB nanoparticles within a reverse micellar system

Example 8: Microscopic Characterization of In Situ Prepared and Stabilized PB Nanoparticles in the Reverse Micellar System Sample A was analyzed by microscopy (TEM) to highlight the nanoparticles presence and structure. The microscopic pictures are shown in FIG. 5. Under conditions of the invention, particles smaller than 5 nm are discernable. Particles higher than 5 nm should have been clearly visible, thus the present nanoparticles in Sample A have a diameter ranging from 1 to 5 nm.

Example 9: In Vitro Cesium Adsorption Study Using Commercial or In Situ Prepared PB Nanoparticles in the Reverse Micellar System An in vitro study was achieved with two different systems. The purpose was to compare the efficiency of cesium absorption on different PB nanoparticles.

The first system tested is comparative and is a surrogate of Radiogardase® using available commercial PB within a reverse micellar system.

The second system tested comprises PB nanoparticles prepared and stabilized in a reverse micellar system according to the invention.

Preparation of Sample I 30.00 g of commercially available lecithin, containing more than 97% of phosphatidylcholine, were dissolved in 26.00 g of absolute ethanol under magnetic stirring at 300 r/min and room temperature. Then 5.00 g of beta-sitosterol were dissolved in the mixture in the same conditions. 129.00 g of Peceol® were added thereto and magnetic stirring was carried out at 700 r/min and 37° C. to form on oily homogenous phase. Eventually, 10.00 g of water for HPLC were added to form a homogenous reverse micellar system. Then, 0.04 g of commercial PB was dispersed in the homogenous reverse micellar system at room temperature and vortexed.

Preparation of Sample J

J1: 0.11 g of commercially available ferric chloride hexahydrate, with purity above 97%, was dissolved in 9.89 g of water for HPLC at room temperature after 10 seconds of vortex.

J2: 15.00 g of commercially available lecithin, containing more than 97% of phosphatidylcholine, were dissolved in 13.00 g of absolute ethanol under magnetic stirring at 300 r/min and room temperature. 2.50 g of beta-sitosterol were dissolved in the mixture in the same conditions. 64.50 g of Peceol® were added thereto and magnetic stirring was carried out at 700 r/min and 37° C. to form an oily homogenous phase.

J3: 5.00 g of J1 were added to 95.00 g of J2 at room temperature and the mixture was vortexed for 10 seconds to achieve an isotropic and homogenous reverse micellar phase containing the first precursor of PB.

J4: 0.15 g of commercially available sodium hexacyanoferrate, with purity above 99%, was dissolved in 9.85 g of water for HPLC at room temperature after 10 seconds of vortex.

J5: 15.00 g of commercially available lecithin, containing more than 97% of phosphatidylcholine, were dissolved in 13.00 g of absolute ethanol under magnetic stirring at 300 r/min and room temperature. 2.50 g of beta-sitosterol were dissolved in the mixture in the same conditions. 64.50 g of Peceol® were added thereto and magnetic stirring was carried out at 700 r/min and 37° C. to form an oily homogenous phase.

J6: 5.00 g of J4 were added to 95.00 g of J5 at room temperature and the mixture was vortexed for 10 seconds to achieve an isotropic and homogenous reverse micellar phase containing the second precursor of PB.

J: 100.00 g of J3 and 100.00 g of J6 were together vortexed for 10 seconds at room temperature to obtain spontaneously in situ nanoparticles formation of PB.

Preparation of Cesium-containing Samples K

Figure 6:
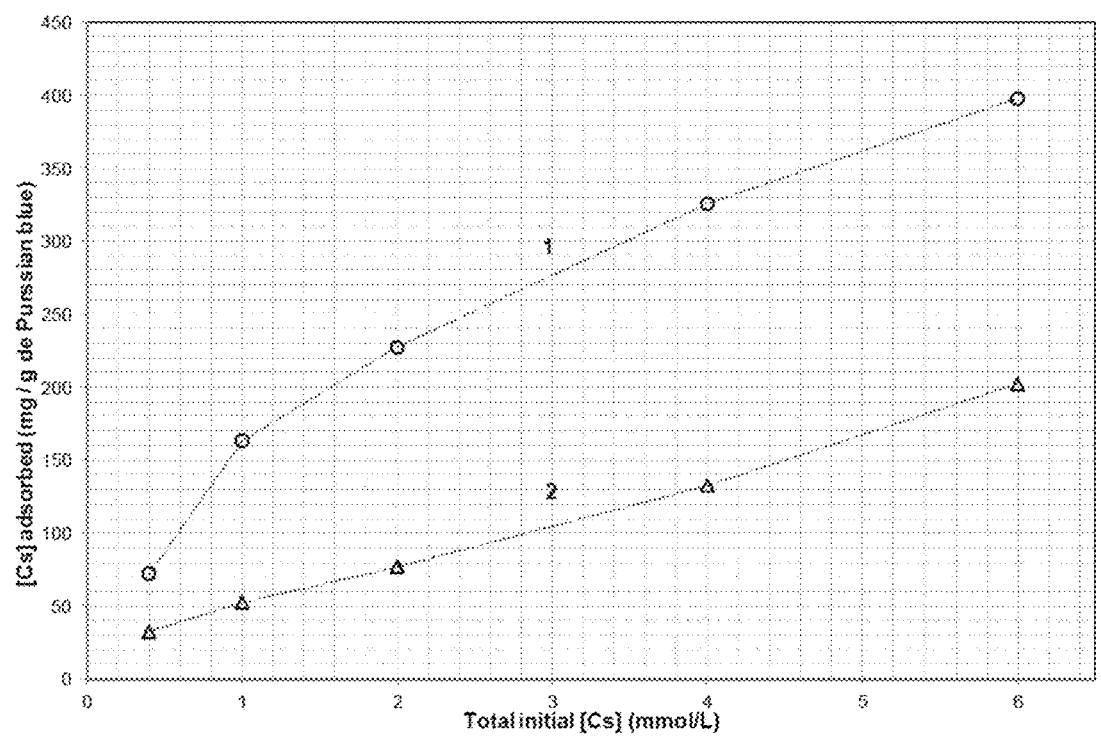
FIG. 6: $Cs^+$ isotherm for reverse micellar system containing (1) in situ prepared PB nanoparticles according to the invention and (2) commercial PB

K1: 0.4 mol·L$^{-1}$ of $Cs^+$ was prepared by dissolving 0.004 g of CsCl, with purity above 99%, in 44.996 g of water for HPLC K2: 1.0 mol·L$^{-1}$ of $Cs^+$ was prepared by dissolving 0.008 g of CsCl, with purity above 99%, in 44.992 g of water for HPLC K3: 2.0 mol·L$^{-1}$ of $Cs^+$ was prepared by dissolving 0.016 g of CsCl, with purity above 99%, in 44.984 g of water for HPLC K4: 4.0 mol·L$^{-1}$ of $Cs^+$ was prepared by dissolving 0.034 g of CsCl, with purity above 99%, in 44.966 g of water for HPLC K5: 6.0 mol·L$^{-1}$ of $Cs^+$ was prepared by dissolving 0.050 g of CsCl, with purity above 99%, in 44.950 g of water for HPLC The experience consisted in contacting 24.00 g of samples I and J with 7.00 g of each of the five samples K. It induced biphasic systems which were mixed continuously for 24 hours in closed vessels. After 24 h stirring, all the biphasic systems were centrifuged to recover the aqueous phases containing the remaining cesium ions. Then, cesium concentrations were analyzed using ionic chromatography in order to show the sorption of cesium for different initial Cs concentrations, the so-called isotherms showed in FIG. 6. The results show that in situ prepared and stabilized PB nanoparticles are more efficient than commercial PB for adsorbing cesium.

The following Table 1 summarizes the samples as detailed above:

| Sample | First precursor(s) | Second precursor(s) | Nanoparticle Short Formula |
|---|---|---|---|
| In situ synthesis of cyano-bridged metal nanoparticles | | | |
| A | $FeCl_3$, $6H_2O$ | $Na_4[Fe(CN)_6]$, $10H_2O$ | $Fe[Fe(CN)_6]$ |
| B | $ZnCl_2$, $4H_2O$ | $K_3[Fe(CN)_6]$ | $Zn[Fe(CN)_6]$ |
| C | $MnCl_2$, $4H_2O$ | $K_3[Fe(CN)_6]$ | $Mn[Fe(CN)_6]$ |
| D (5%) | 5% $MnCl_2$ + 95% $FeCl_3$ | $Na_4[Fe(CN)_6]$, $10H_2O$ | $MnFe[Fe(CN)_6]$ |

-continued

| Sample | First precursor(s) | Second precursor(s) | Nanoparticle Short Formula |
|---|---|---|---|
| D (10%) | 10% MnCl$_2$ + 90% FeCl$_3$ | Na$_4$[Fe(CN)$_6$], 10H$_2$O | MnFe[Fe(CN)$_6$] |
| D (25%) | 25% MnCl$_2$ + 75% FeCl$_3$ | Na$_4$[Fe(CN)$_6$], 10H$_2$O | MnFe[Fe(CN)$_6$] |
| D (50%) | 50% MnCl$_2$ + 50% FeCl$_3$ | Na$_4$[Fe(CN)$_6$], 10H$_2$O | MnFe[Fe(CN)$_6$] |
| D (75%) | 75% MnCl$_2$ + 25% FeCl$_3$ | Na$_4$[Fe(CN)$_6$], 10H$_2$O | MnFe[Fe(CN)$_6$] |
| E | 50% MnCl$_2$ + 50% ZnCl$_2$ | K$_3$[Fe(CN)$_6$] | MnZn[Fe(CN)$_6$] |
| F | FeCl$_3$, 6H$_2$O | K$_2$[Ni(CN)$_4$] | Fe[Ni(CN)$_6$] |
| G | FeCl$_3$, 6H$_2$O | [Mo or W](CN)$_8$ | Fe[Mo(CN)$_6$] |
| H | Gd(NO$_3$)$_3$, 6H$_2$O | K$_3$[Fe(CN)$_6$] | Gd[Fe(CN)$_6$] |

In vitro study of cesium absorption on cyano-bridged metal nanoparticles

| | | | |
|---|---|---|---|
| I | | | Fe[Fe(CN)$_6$] Commercial PB |
| J | FeCl$_3$ | Na$_4$[Fe(CN)$_6$] | Fe[Fe(CN)$_6$] |
| K | Cesium chloride aqueous solutions | | |

Example 10: In Vivo Study of Cesium Decorporation with In Situ Prepared PB Cyano-Bridged Metal Nanoparticles in the Reverse Micellar System Preparation of Sample L L1: 0.17 g of commercially available ferric chloride hexahydrate, with purity above 97%, was dissolved in 3.83 g of water for HPLC at room temperature after 10 seconds of vortex.

L2: 3.60 g of commercially available lecithin, containing more than 97% of phosphatidylcholine, were dissolved in 3.24 g of absolute ethanol under magnetic stirring at 300 r/min and room temperature. 0.90 g of beta-sitosterol was dissolved in the mixture in the same conditions. 26.10 g of Peceol® were added thereto and magnetic stirring was carried out at 700 r/min and 37° C. to form a homogenous oil-based phase.

L3: 2.16 g of L1 were added to 33.84 g of L2 at room temperature and the mixture was vortexed for 10 seconds to achieve an isotropic and homogenous reverse micellar phase containing the first precursor of PB.

L4: 0.23 g of commercially available sodium hexacyanoferrate(II) decahydrate, with purity above 99%, was dissolved in 3.77 g of water for HPLC at room temperature after 10 seconds of vortex.

L5: 3.60 g of commercially available lecithin, containing more than 97% of phosphatidylcholine, were dissolved in 3.24 g of absolute ethanol under magnetic stirring at 300 r/min and room temperature. 0.90 g of beta-sitosterol was dissolved in the mixture in the same conditions. 26.10 g of Peceol® were added thereto and magnetic stirring was carried out at 700 r/min and 37° C. to form an homogenous oil-based phase.

L6: 2.16 g of L4 were added to 33.84 g of L5 at room temperature and the mixture was vortexed for 10 seconds to achieve an isotropic and homogenous reverse micellar phase containing the second precursor of PB.

L: 35.00 g of L3 and 35.00 g of L6 were together vortexed for 10 seconds at room temperature to obtain spontaneously in situ nanoparticles formation of PB.

Preparation of Sample M

M1: 0.34 g of commercially available ferric chloride hexahydrate, with purity above 97%, was dissolved in 3.66 g of water for HPLC at room temperature after 10 seconds of vortex.

M2: 1.20 g of commercially available lecithin, containing more than 97% of phosphatidylcholine, was dissolved in 1.08 g of absolute ethanol under magnetic stirring at 300 r/min and room temperature. 0.30 g of beta-sitosterol was dissolved in the mixture in the same conditions. 8.70 g of Peceol® were added thereto and magnetic stirring was carried out at 700 r/min and 37° C. to form a homogenous oil-based phase.

M3: 0.72 g of M1 was added to 11.28 g of M2 at room temperature and the mixture was vortexed for 10 seconds to achieve an isotropic and homogenous reverse micellar phase containing the first precursor of PB.

M4: 0.45 g of commercially available sodium hexacyanoferrate(II) decahydrate, with purity above 99%, was dissolved in 3.55 g of water for HPLC at room temperature after 10 seconds of vortex.

M5: 1.20 g of commercially available lecithin, containing more than 97% of phosphatidylcholine, was dissolved in 1.08 g of absolute ethanol under magnetic stirring at 300 r/min and room temperature. 0.30 g of beta-sitosterol was dissolved in the mixture in the same conditions. 8.70 g of Peceol® were added thereto and magnetic stirring was carried out at 700 r/min and 37° C. to form a homogenous oil-based phase.

M6: 0.72 g of M4 was added to 11.28 g of M5 at room temperature and the mixture was vortexed for 10 seconds to achieve an isotropic and homogenous reverse micellar phase containing the second precursor of PB.

M: 10.00 g of M3 and 10.00 g of M6 were together vortexed for 10 seconds at room temperature to obtain spontaneously in situ nanoparticles formation of PB.

Materials and Methods

After the 3-days acclimatization, 16 Sprague-Dawley outbreed rats of about 7-8 week-old at the beginning of treatments (i.e. 250+/−30 g body weight) were placed in individual metabolism cages to allow separated collection of urine and feces, with a constant temperature of 22° DC and a daily diet comprising AO4C granulates from S.A.F.E. and ad libitum tap water.

All the rats were contaminated using an intra peritoneal administration of 500 µg of cesium. The treatments begin one hour after Cs contamination (except for the untreated rats of group A); the rats were then administered for 4 days with sample L once a day (group B) and twice a day (group D) or sample M twice a day (group C). For buccal and rectal routes, the rats were anaesthetized under gaseous isoflurane to ensure a more reproducible administration.

Urines and feces for each rat were separately and cumulatively collected for 4 days and the cesium doses were analyzed by the ICP-MS technique after mineralization.

The following Table 2 shows the corresponding study plan of this in vivo study:

| Groups | A | B | C | D |
|---|---|---|---|---|
| Number of rats | 4 | 4 | 4 | 4 |
| Decorporant identification | | Sample L | Sample M | Sample L |
| Route | | Gavage | Buccal | Rectal |
| Concentration of the PB nanoparticles | | 1 mg/g | 2 mg/g | 1 mg/g |
| Dose per administration | | 8 mg/kg | 2 mg/kg | 1 mg/kg |
| Duration | | once a day for 4 consecutive days | twice a day for 4 consecutive days | twice a day for 4 consecutive days |

-continued

| Groups | A | B | C | D |
|---|---|---|---|---|
| Cumulated dose received by rat of 250 g | | 8 mg | 4 mg | 2 mg |

Figure 7:
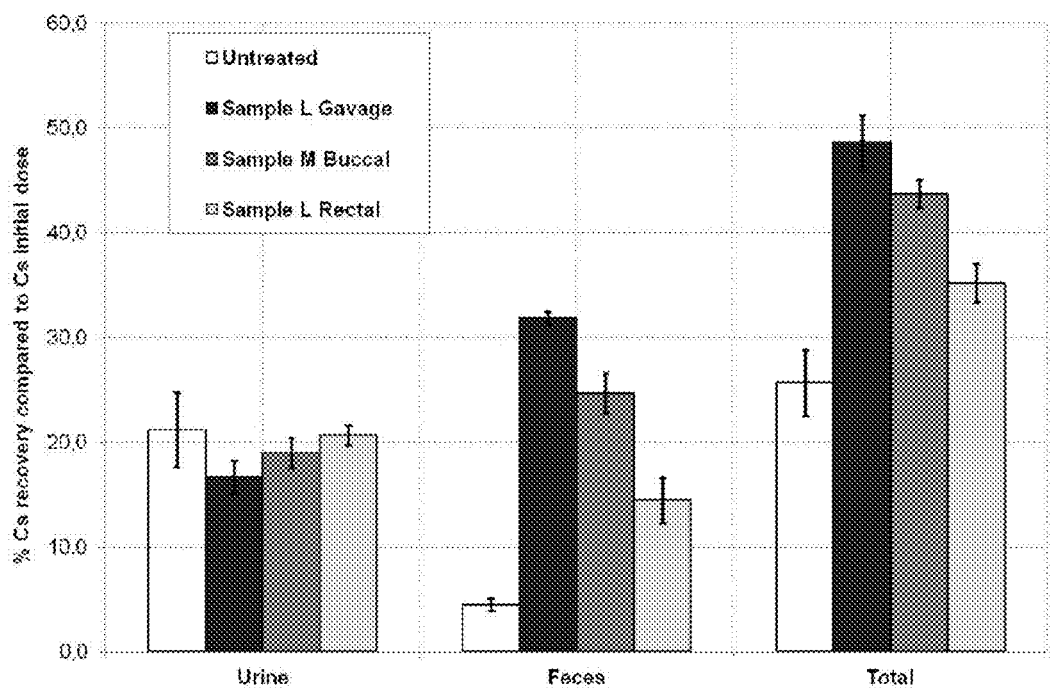
FIG. 7: % recovered $Cs^+$ at 4 days compared to $Cs^+$ initial dose of 0.5 mg per rat in urine and feces for 4 groups (Mean on 4 rats): Untreated, Sample L Gavage, Sample M Buccal and Sample L Rectal with a cumulative decorporating PB dose of 0-8-4-2 mg, respectively (The standard error to the mean is represented by error bars)

The percentages of recovered cesium in excreta for each group are showed in the FIG. 7.

It shows that the PB nanoparticles formulated within the reverse micellar system enhance the excretion of cesium in the feces. Le Gall et al. described close efficacy results with lower Cs contamination and higher PB doses (Legall, 2006). It suggests that the cyano-bridged metal nanoparticles of PB in situ prepared according to the invention allow an improvement of cesium decorporation with lower PB dose.

Example 11: In Vivo Study of Cesium Decorporation with In Situ Prepared PB Cyano-Bridged Metal Nanoparticles in the Reverse Micellar System in Comparison with Commercially Available PB Preparation of Sample N
N1: 6.00 g of commercially available lecithin, containing more than 97% of phosphatidylcholine, were dissolved in 5.40 g of absolute ethanol under magnetic stirring at 300 r/min and room temperature. 1.50 g of beta-sitosterol was dissolved in the mixture in the same conditions. 43.50 g of Peceol® were added thereto and magnetic stirring was carried out at 700 r/min and 37° C. to form a homogenous oil-based phase.
N: 3.60 g of water for HPLC were added to 56.40 g of N1 at room temperature and the mixture was vortexed for 10 seconds to achieve an isotropic and homogenous reverse micellar phase without any active ingredients.

Preparation of Samples O, P, Q, R
O, P, Q, R are prepared by suspension of available commercial PB in distilled water. All the samples are placed under magnetic stirring for 30 minutes to obtain PB suspensions of 0.5-1-2-10 mg/g respectively.

Preparation of Sample S
S1: 0.06 g of commercially available ferric chloride hexahydrate, with purity above 97% was dissolved in 2.94 g of water for HPLC at room temperature after 10 second of vortex.
S2: 3.20 g of commercially available lecithin, containing more than 97% of phosphatidylcholine, were dissolved in 2.88 g of absolute ethanol under magnetic stirring at 300 r/min and room temperature. 0.80 g of beta-sitosterol was dissolved in the mixture in the same conditions. 23.20 g of Peceol® were added thereto and magnetic stirring was carried out at 700 r/min and 37° C. to form a homogenous oil-based phase.
S3: 1.92 g of S1 was added to 30.08 g of S2 at room temperature and the mixture was vortexed for 10 seconds to achieve an isotropic and homogenous reverse micellar phase containing the first precursor of PB
S4: 0.09 g of commercially available sodium hexacyanoferrate(II) decahydrate, with purity above 99%, was dissolved in 2.91 g of water for HPLC at room temperature after 10 seconds of vortex.
S5: 3.20 g of commercially available lecithin, containing more than 97% of phosphatidylcholine, were dissolved in 2.88 g of absolute ethanol under magnetic stirring at 300 r/min and room temperature. 0.80 g of beta-sitosterol was dissolved in the mixture in the same conditions. 23.20 g of Peceol® were added thereto and magnetic stirring was carried out at 700 r/min and 37° C. to form a homogenous oil-based phase.
S6: 1.92 g of S4 was added to 30.08 g of S5 at room temperature and the mixture was vortexed for 10 seconds to achieve an isotropic and homogenous reverse micellar phase containing the second precursor of PB.
S: 30.00 g of S3 and 30.00 g of S6 were together vortexed for 10 seconds at room temperature to obtain spontaneously in situ nanoparticles formation of PB.

Preparation of Sample T
T1: 0.12 g of commercially available ferric chloride hexahydrate, with purity above 97% was dissolved in 2.88 g of water for HPLC at room temperature after 10 second of vortex.
T2: 3.20 g of commercially available lecithin, containing more than 97% of phosphatidylcholine, were dissolved in 2.88 g of absolute ethanol under magnetic stirring at 300 r/min and room temperature. 0.80 g of beta-sitosterol was dissolved in the mixture in the same conditions. 23.20 g of Peceol® were added thereto and magnetic stirring was carried out at 700 r/min and 37° C. to form a homogenous oil-based phase.
T3: 1.92 g of T1 was added to 30.08 g of T2 at room temperature and the mixture was vortexed for 10 seconds to achieve an isotropic and homogenous reverse micellar phase containing the first precursor of PB
T4: 0.18 g of commercially available sodium hexacyanoferrate(II) decahydrate, with purity above 99%, was dissolved in 2.82 g of water for HPLC at room temperature after 10 seconds of vortex.
T5: 3.20 g of commercially available lecithin, containing more than 97% of phosphatidylcholine, were dissolved in 2.88 g of absolute ethanol under magnetic stirring at 300 r/min and room temperature. 0.80 g of beta-sitosterol was dissolved in the mixture in the same conditions. 23.20 g of Peceol® were added thereto and magnetic stirring was carried out at 700 r/min and 37° C. to form a homogenous oil-based phase.
T6: 1.92 g of T4 was added to 30.08 g of T5 at room temperature and the mixture was vortexed for 10 seconds to achieve an isotropic and homogenous reverse micellar phase containing the second precursor of PB.
T: 30.00 g of T3 and 30.00 g of T6 were together vortexed for 10 seconds at room temperature to obtain spontaneously in situ nanoparticles formation of PB.

Preparation of Sample U
U1: 0.24 g of commercially available ferric chloride hexahydrate, with purity above 97% was dissolved in 2.76 g of water for HPLC at room temperature after 10 second of vortex.
U2: 3.20 g of commercially available lecithin, containing more than 97% of phosphatidylcholine, were dissolved in 2.88 g of absolute ethanol under magnetic stirring at 300 r/min and room temperature. 0.80 g of beta-sitosterol was dissolved in the mixture in the same conditions. 23.20 g of Peceol® were added thereto and magnetic stirring was carried out at 700 r/min and 37° C. to form a homogenous oil-based phase.
U3: 1.92 g of U1 was added to 30.08 g of U2 at room temperature and the mixture was vortexed for 10 seconds to achieve an isotropic and homogenous reverse micellar phase containing the first precursor of PB
U4: 0.36 g of commercially available sodium hexacyanoferrate(II) decahydrate, with purity above 99%, was dissolved in 2.64 g of water for HPLC at room temperature after 10 seconds of vortex.

U5: 3.20 g of commercially available lecithin, containing more than 97% of phosphatidylcholine, were dissolved in 2.88 g of absolute ethanol under magnetic stirring at 300 r/min and room temperature. 0.80 g of beta-sitosterol was dissolved in the mixture in the same conditions. 23.20 g of Peceol® were added thereto and magnetic stirring was carried out at 700 r/min and 37° C. to form a homogenous oil-based phase.

U6: 1.92 g of U4 was added to 30.08 g of U5 at room temperature and the mixture was vortexed for 10 seconds to achieve an isotropic and homogenous reverse micellar phase containing the second precursor of PB.

U: 30.00 g of U3 and 30.00 g of U6 were together vortexed for 10 seconds at room temperature to obtain spontaneously in situ nanoparticles formation of PB.

Materials and Methods

After the 3-days acclimatization, 45 Sprague-Dawley outbreed rats of about 7-8 week-old at the beginning of treatments (i.e. 250+/−g body weight) were placed in individual metabolism cages to allow separated collection of feces, with a constant temperature of 22° DC and a daily diet comprising AO4C granulates from S.A.F.E. and ad libitum tap water.

All the rats were contaminated using an intra peritoneal administration of 50 μg of cesium. The treatments begin three hours after Cs contamination; the rats were then orally administered by gavage twice a day for four consecutive days with distilled water (group A), sample N (group B), sample O (group C), sample P (group D), sample Q (group E), sample R (group F), sample S (group G), sample T (group H), sample U (group I).

The feces of each rat were separately and cumulatively collected on 48 h period (from 0 to 48 h and 48 h to 96 h). The hearts were collected at sacrifice at the end of the treatment.

The cesium doses of feces and hearts were analyzed by the ICP-MS technique after mineralization.

Figure 9:
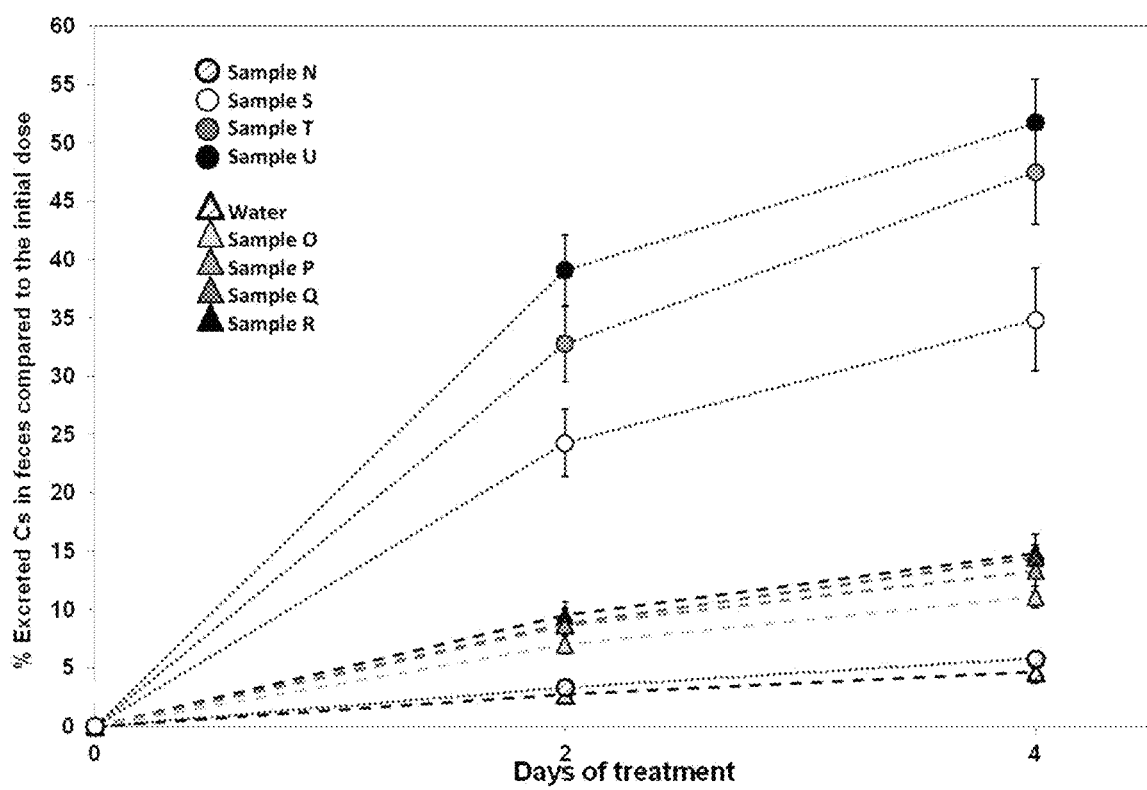
FIG. 9: % recovered $Cs^+$ at 2 and 4 days compared to $Cs^+$ initial dose of 0.05 mg per rat in feces for 9 groups (mean on 5 rats): Water, Samples O, P, Q & R with a cumulative decorporating PB dose of 4-8-16-80 mg per rat respectively and Samples N, S, T & U with a cumulative decorporating PB dose of 0-4-8-16 mg per rat respectively (The standard error to the mean is represented by error bars)

The following Table 3 summarizes the study plan of this in vivo study:

The percentages of recovered cesium in feces for each group are showed in the FIG. 9.

It confirms that, at the same dosage, the cesium decorporation is more efficient with cyano-bridged metal nanoparticles of PB in situ prepared according to the invention compared to available commercial PB in suspension in distilled water.

Furthermore, the rate of cesium decorporation is higher at 48 h with cyano-bridged metal nanoparticles of PB prepared in situ according to the invention compared to commercially available PB in suspension in distilled water.

REFERENCES

S. S. Atik and J. K. Thomas (1981) Transport of photoreduced ions in water in oil microemulsions: movement of ions from one water pool to another. J. Am. Chem. Soc. 103, 3543-3550

P. Barnickel and A. Wokaun (1990) Synthesis of Metal Colloids in Inverse Microemulsions. Molecular Physics, Vol. 69, No. 1, pp. 1-9.

H. J. Buser and A. Ludi and W. Petter and D. Schwarzenbach (1972) Single crystal study of Prussian Blue: Fe4[Fe(CN)6]2, 14H2O. J. C. S. Chem. Comm.

E. Chelebaeva, Y. Guari, J. Larionova, A. Trifonov and C. Guerin (2008) Soluble Ligand-Stabilized Cyano-Bridged Coordination Polymer Nanoparticles. Chem. Mater., 20, 1367-1375

C. A. Chugh and D. Bharti (2012) Open Journal of Synthesis Theory and Applications, 1, 23-30

G. Clavel, J. Larionova, Y. Guari and C. Guerin (2006) Synthesis of Cyano-Bridged Magnetic Nanoparticles Using Room-Temperature Ionic Liquids. Chem. Eur. J., 12, 3798-3804

I. Danielsson and B. Lindman (1981) The definition of microemulsion. Colloids and Surface, 3, 391-392

T. A. Denisova, L. G. Maksimova, O. N. Leonidova, and N. A. Zhuravlev (2009) Physical and Chemical Properties of Zinc Cyanoferrates(II). Russian Journal of Inorganic Chemistry, 2009, Vol. 54, No. 1, pp. 6-12. © Pleiades Publishing, Ltd

| Groups | A | B | C | D | E | F | G | H | I |
|---|---|---|---|---|---|---|---|---|---|
| Number of rats | 5 | 5 | 5 | 5 | 5 | 5 | 5 | 5 | 5 |
| Decorporant identification | Distilled water | Sample N | Sample O | Sample P | Sample Q | Sample R | Sample S | Sample T | Sample U |
| Route | | | | | Gavage | | | | |
| Concentration of the PB nanoparticles | | | 0.5 mg/g | 1 mg/g | 2 mg/g | 10 mg/g | 0.5 mg/g | 1 mg/g | 2 mg/g |
| Dose per administration | | | 2 mg/kg | 4 mg/kg | 8 mg/kg | 40 mg/kg | 2 mg/kg | 4 mg/kg | 8 mg/kg |
| Duration | | | Twice a day for 4 consecutive days | | | | | | |
| Cumulated dose received after treatment by rat of 250 g | | | 4 mg | 8 mg | 16 mg | 80 mg | 4 mg | 8 mg | 16 mg |

Figure 8:
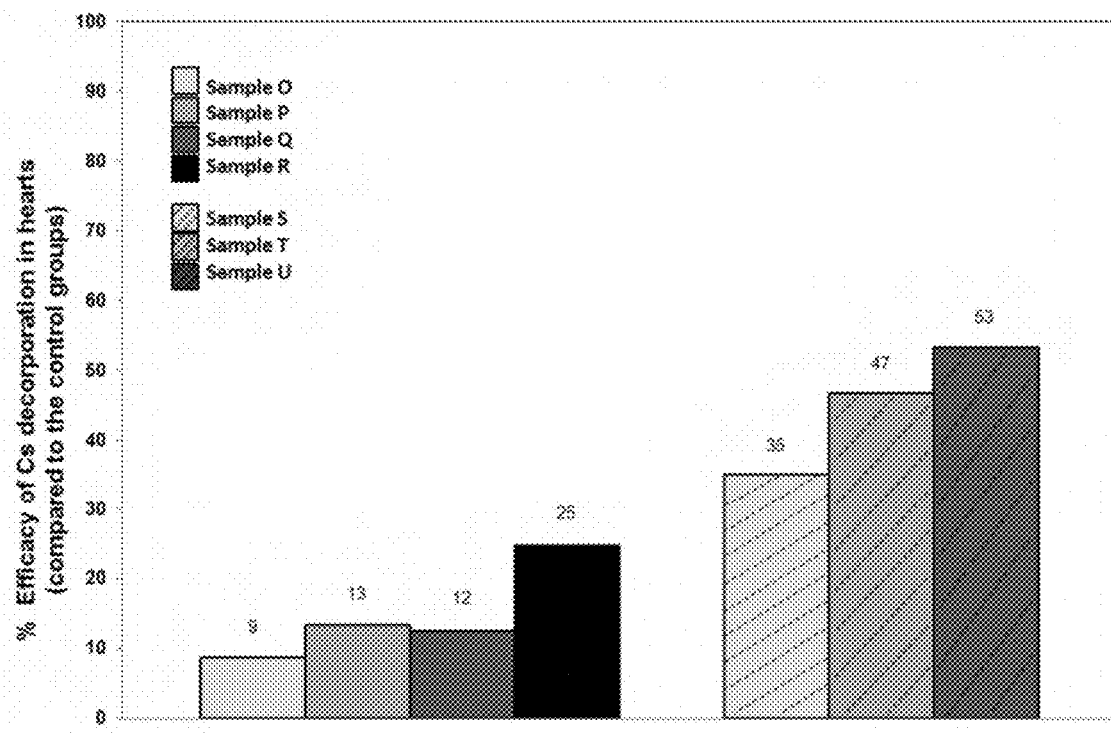
FIG. 8: % efficacy of $Cs^+$ decorporation in heart compared to the control groups for 7 groups treated by gavage (mean on 5 rats): Samples O, P, Q & R with a cumulative decorporating PB dose of 4-8-16-80 mg per rat respectively and Samples S, T & U with a cumulative decorporating PB dose of 4-8-16 mg per rat respectively (The standard error to the mean is represented by error bars)

The percentages of efficacy of decorporation in hearts for each group are showed in the FIG. 8.

It shows that chronic treatment with PB nanoparticles reduced the heart retention of cesium compared to control (0% efficacy). Furthermore, at the same dosage, the cyano-bridged metal nanoparticles of PB in situ prepared according to the invention have a greater efficacy (from 35 to 53%) than the available commercial PB in suspension in distilled water (from 9 to 12%).

J. Eastoe, M. J. Hollamby and L. Hudson (2006) Recent advances in nanoparticle synthesis with reversed micelles. Advances in Colloid and Interface Science, 128-130, 5-15

D. Ellis, M. Eckhoff and V. D. Neff (1981) Electrochromism in the Mixed-Valence Hexacyanides. 1. Voltammetric and Spectral Studies of the Oxidation and Reduction of Thin Films of Prussian Blue. J. Phys. Chem., 85, 1225-1231

R. Farina, C E Brandao-Mello and A R Oliveira (1991) Medical aspects of $^{137}$Cs decorporation: the Goiania radiological accident. Health Phys.; 60:63-6

P. D. I. Fletcher, A. M. Howe and B. H. Robinson (1987) The Kinetics of Solubilisate Exchange between Water Droplets of a Water-in-oil Microemulsion. J. Chem. SOC., Faraday Trans. I, 83, 985-1006

S. N. Ghosh (1974) Infrared spectra of the prussian blue analogs. J. inorg. nuel. Chem., Vol. 36, pp. 2465-2466. Pergamon Press.

Y. Guo and A. R. Guadalupe (1999) Chemically Derived Prussian Blue Sol-Gel Composite Thin Films. Chem. Mater., 11, 135-140

M. H. Hengé-Napoli, G. N. Stradling, D. M. Taylor (2000). Decorporation of Radionuclides from the Human Body. Radiat Prot Dosim (Special Issue), 87(1). Commission of the European Communities Report EUR 19330

J. D. Holmes, P. A. Bhargava, B. A. Korgel and K. P. Johnston (1999) Synthesis of Cadmium Sulfide Q Particles in Water-in-CO2 Microemulsions. Langmuir, 15, 6613-6615

S. S. Kaye and J. R. Long (2006) The role of vacancies in the hydrogen storage properties of Prussian blue analogues. Catalysis Today 120, 311-316

J. F. Keggin and F. D. Miles (1936) Structures and Formulæ of the Prussian Blues and Related Compounds. Nature 137, 577-578

K. J. Klabunde, editor. Nanoscale Materials in Chemistry, 1st edn. New York:Wiley Interscience, 2001

J. Larionova, Y. Guari, C. Sangregorio and C. Guerin (2009) Cyano-bridged coordination polymer nanoparticles. New J. Chem., 33, 1177-1190-1177

B. Le Gall, F. Tran, D. Renault, J.-C. Wilk and E. Ansoborlo (2006) Comparison of Prussian blue and apple-pectin effacy on 137Cs decorporation in rats, Biochimie 88, 1837-1841

Z. Li, J. Zhang, T. Mu, J. Du, Z. Liu, B. Han and J. Chen (2004) Preparation of polyvinylpyrrolidone-protected Prussian blue nanocomposites in microemulsion, Colloids and Surfaces A: Physiochem. Eng. Aspects 243, 63-66

M. Li, C. Deng, C. Chen, L. Peng, G. Ning, Q. Xie and S. Yao (2006) An Amperometric Hydrogen Peroxide Biosensor Based on a Hemoglobin-Immobilized Dopamine-Oxidation Polymer/Prussian Blue/Au Electrode. Electroanalysis 18, No. 22, 2210-2217

M. A. Lopez-Quintela, J. Rivas, M. C. Blanco and C. Tojo (2003) Synthesis of nanoparticles in microemulsions. Nanoscale Materials, pp 135-155

M. A. Lopez-Quintela (2003b) Synthesis of nanomaterials in microemulsions: formation mechanisms and growth control. Current Opinion in Colloid and Interface Science, 8, 137-144

A. Ludi, H.-U. Gudel and M. Ruegg (1970) The Structural Chemistry of Prussian Blue Analogs. A Single-Crystal Study of Manganese(II) Hexacyanocobaltate(III), Mn3[Co(CN)6],xH2O. Inorganic Chemistry, Vol. 9, No. 10, 2225

F. Ma, J. Lu, Z. Wang, J. Sun, Q. Gong, B. Song, H. Ai and Z. Gu (2010) Encapsulation of MnFe2O4 Nanoparticles with Amphiphilic PEG-Lipid Micelles as Novel MRI Probes. International Journal of Magnetic Resonance Imaging Vol. 02, No. 01, pp. 050-055

C. A. Massaad and R. G. Pautler (2011) Manganese-Enhanced Magnetic Resonance Imaging (MEMRI). Methods Mol Biol.; 711: 145-174.

J. W. McCargar and V. D. Neff (1988) Thermodynamics of Mixed-Valence Intercalation Reactions: The Electrochemical Reduction of Prussian Blue. J. Phys. Chem., 92, 3598-3604

A. M. Mohs and Z.-R. Lu (2007) Gadolinium(III)-based blood-pool contrast agents for magnetic resonance imaging: status and clinical potential. Expert Opin. Drug Deliv., 4(2):149-164

J. Nesamony and W. M. Kolling (2005) IPM/DOSS/Water Microemulsions as Reactors for Silver Sulfadiazine Nanocrystal Synthesis. Journal pf pharmaceutical sciences, Vol. 94, No. 6

H. Noritomi, S. Miyagawa, N. Igari, H. Saito and S. Kato (2013) Application of Reverse Micelles of Alkyl Glucosides to Synthesis of Silver Nanoparticles. Advances in Nanoparticles, 2, 344-349

Y. Okumura (1998) Organic Solvents and Surfactants for Toxicity Test Using Aquatic Organisms and Their Acceptable Concentrations. Bulletin of the National Research Institute of Fisheries Science, Vol. 11, No. 11, pp. 113-134.

D. Pan, A. H. Schmieder, S. A. Wickline and G. M. Lanza (2011) Manganese-based MRI contrast agents: past, present and future. Tetrahedron., 67(44): 8431-8444

D. Papanikoalou, W. Kosaka, S. Margadonna, H. Kagi, S. Ohkoshi and K. Prassides (2007) Piezomagnetic Behavior of the Spin Crossover Prussian Blue Analogue CsFe[Cr(CN)6]. J. Phys. Chem. C, 111 (22), pp 8086-8091

M. Perrier, S. Kenouche, J. Long, K. Thangavel, J. Larionova, C. Goze-Bac, A. Lascialfari, M. Mariani, N. Baril, C. Guerin, B. Donnadieu, A. Trifonov and Y. Guari (2013) Investigation on NMR Relaxivity of Nano-Sized Cyano-Bridged Coordination Polymers, Inorg. Chem., 52, 13402-13414

M. P. Pileni (1993) Reverse micelles as microreactors. J. Phys. Chem., 97 (27), pp 6961-6973

M. P. Pileni (1997) Nanosized particles made in colloidal assemblies. Langmuir, 13, 3266-3276

M. P. Pileni (2007) Self-assembly of inorganic nanocrystals: Fabrication and collective intrinsic properties. Acc. Chem. Res., 40, 685-693

L. Qi (2006) Synthesis of inorganic nanostructure in reverse micelles. Encyclopedia of Surface and Colloid Science, Taylor & Francis.

R. E. Riter, E. P. Undiks and N. E. Levinger (1998) Impact of Counterion on Water Motion in Aerosol OT Reverse Micelles. J. Am. Chem. Soc., 120, 6062-6067

H. Saito and K. Shinoda (1967) The solubilization of hydrocarbons in aqueous phases of nonionic surfactants. J. Colloid Interface Sci. Vol. 24, No. 1, pp. 10

O. Sato, S. Hayami, Y. Einaga and Z. Gu (2003) Control of the Magnetic and Optical Properties in MolecularCompounds by Electrochemical, Photochemical and Chemical Methods. Bull. Chem. Soc. Jpn., 76, 443-470

O. Sato (2007) Electrochromism and electrochemical magnetism in Ni—Fe Prussian blue. Journal of Solid State Electrochemistry, Vol. 11, Issue 6, pp 773-779

W. Stevens, C. Van Peteghem, A. Heyndrickx and F. Barbier (1974) Eleven cases of thallium intoxication treated with Prussian blue, Int. J. Clin. Pharmacol.; 10:1-22

N. L. Torad, M. Hu, M. Imura, M. Naito and Y. Yamauchi (2012) Large Cs adsorption capability of nanostructured Prussian Blue particles with high accessible surface areas. J. Mater. Chem., 22, 18261

T. Uemura, M. Ohba and S. Kitagawa (2004) Size and Surface Effects of Prussian Blue Nanoparticles Protected by Organic Polymers. Inorg. Chem., 43 (23), pp 7339-7345

S. Vaucher, M. Li and S. Mann (2000) Synthesis of Prussian blue nanoparticles and nanocrystal superlattices in reverse microemulsions, Angew. Chem. 112, 1863-1866

M. Verdaguer and G. Girolami (2004) Magnetism: Molecules to Materials V. Edited by J. S. Miller and M. Drillon, Wiley VCH Verlag GmbH & Co. KGaA, Weinheim T. Vincent, C. Vincent, Y. Barre, Y. Guari, G. Le Saout and E. Guibal (2014) Immobilization of metal hexacyanoferrates in chitin beads for cesium sorption: synthesis and characterization. J. Mater. Chem. A, 2, 10007

G. Wang, J. Zhou and J. Li (2007) Layer-by-layer self-assembly aluminum Keggin ions/Prussian blue nanoparticles ultrathin films towards multifunctional sensing applications. Biosensors and Bioelectronics, 22, 2921-2925

M. Yamada, M. Arai, M. Kurihara, M. Sakamoto and M. Miyake (2004) Synthesis and Isolation of Cobalt Hexacyanoferrate/Chromate Metal Coordination Nanopolymers Stabilized by Alkylamino Ligand with Metal Elemental Control. J. Am. Chem. Soc., 126, 9482-9483

Z. Zhou and Z. Lu (2013) Gadolinium-Based Contrast Agents for MR Cancer Imaging. Wiley Interdiscip Rev Nanomed Nanobiotechnol.; 5(1): 1-18

W. Zhu, K. Liu, X. Sun, X. Wang, Y. Li, L. Cheng and Z. Liu (2015) $Mn^{2+}$ doped Prussian blue nanocubes for bimodal imaging and photothermal therapy with enhanced performance. ACS Appl. Mater. Interfaces

The invention claimed is:

1. A method for the preparation of biocompatible reverse micellar system comprising cyano-bridged metal nanoparticles, comprising:
   mixing (i) at least one biocompatible reverse micellar system comprising at least one acylglycerol, sterol, lecithin, ethanol, and an aqueous solution comprising at least one metal salt, as a precursor, and water,
   with (ii) a biocompatible reverse micellar system comprising at least one acylglycerol, a sterol, lecithin, ethanol, and an aqueous solution comprising a cyano-metalate salt, as a precursor, and water,
   wherein said method is performed without a stabilizing agent, wherein the stabilizing agent is a polyethylene glycol or derivative thereof, or a polysaccharide, and wherein the size of the cyano-bridged metal nanoparticles ranges from 1 nm to 100 nm.

2. The method according to claim 1, wherein the metal salt is a cation with chloride or nitric anions and water molecules.

3. The method according to claim 2, wherein the metallic cation ($M^{p+}$) is a transition metal cation selected from the group consisting of iron, zinc, manganese, and a mixture thereof.

4. The method according to claim 2, wherein the metallic cation ($M^{p+}$) is a transition metal cation selected from the group consisting of gadolinium (Gd), terbium (Tb), ytterbium (Yb), and a mixture thereof.

5. The method according to claim 1, wherein the metallic salt is a metallic chloride or nitric selected from the group consisting of $FeCl_2,4H_2O$; $FeCl_3,6H_2O$; $ZnCl_2,4H_2O$; $MnCl_2,4H_2O$; $Gd(NO_3)_3, 6H_2O$; and a mixture thereof.

6. The method according to claim 1, wherein the cyano-metalate salt is of the formula: $(Alk^+_x[M'(CN)_n]^{q-})$, wherein M' is a metallic cation with CN ligands and $Alk^+$ is an alkali cation, the metallic cation (M') is a transition metal cation, which leads to the number of CN ligands and alkali cations therewith, q is an integer, equal to x; and n is an integer; and x is an integer.

7. The method according to claim 6, wherein the metallic cation (M') is iron, cobalt, nickel or molybdenum or tungsten.

8. The method according to claim 6, wherein the cyano-metalate salt is $Na_4Fe(CN)_6$, $Na_3Fe(CN)_6$, $Na_2Ni(CN)_4$, $Na_4Mo(CN)_8$, or $Na_4W(CN)_8$, wherein sodium can be replaced by potassium.

9. The method according to claim 1, wherein, prior to the mixing step, the (i) and (ii) biocompatible reverse micellar systems are prepared by a method comprising:
   (a) separately preparing aqueous solutions each containing at least one metal precursor by dissolving each metal precursor in water, and
   (b) solubilizing each of the aqueous solutions obtained by (a) within a homogenous oil-based phase comprising at least one acylglycerol, a sterol, lecithin, and ethanol, and optionally water, as to form a homogenous reverse micellar system.

10. A biocompatible reverse micellar system comprising at least one acylglycerol, a sterol, lecithin, ethanol, cyano-bridged metal nanoparticles and water, wherein said system does not comprise a stabilizing agent, wherein the stabilizing agent is a polyethylene glycol or derivative thereof, or a polysaccharide, and wherein the size of the cyano-bridged metal nanoparticles ranges from 1 nm to 100 nm.

11. A biocompatible reverse micellar system obtained by the method according to claim 1.

12. A composition comprising the biocompatible reverse micellar system according to claim 10.

13. A pharmaceutical composition comprising the biocompatible reverse micellar system according to claim 10 in a pharmaceutically acceptable carrier or support.

14. The method according to claim 1, wherein the metal salt is a metallic cation ($M^{p+}$) and is a transitional metal cation or lanthanide cation.

15. The method according to claim 6, wherein q is 2, 3, or 4; n is 4, 6 or 8; and x is 2, 3, or 4.

16. The method according to claim 6, wherein the metallic cation (M') is an iron cation.

17. The method of according to claim 9, wherein the water is deionized water, and the homogenous oil-based phases are the same.

18. The method according to claim 1, wherein the method is carried out from 25° to 40° C.

19. The method according to claim 1, wherein the reverse micellar system comprises from 1 to 30% lecithin, from 0.1 to 20% water and from 30 to 90% acylglycerol, by weight with respect to the total weight of the reverse micellar system.

20. A method for the preparation of biocompatible reverse micellar system comprising cyano-bridged metal nanoparticles, comprising:
   mixing (i) at least one biocompatible reverse micellar system comprising at least one acylglycerol, sterol, lecithin, ethanol, and an aqueous solution comprising at least one metal salt, as a precursor, and water,
   with (ii) a biocompatible reverse micellar system comprising at least one acylglycerol, a sterol, lecithin, ethanol, and an aqueous solution comprising a cyano-metalate salt, as a precursor, and water,
   wherein said method is performed without a stabilizing agent, wherein the stabilizing agent is a compound that stabilizes the size of the nanoparticles, and wherein the size of the cyano-bridged metal nanoparticles ranges from 1 nm to 100 nm.

* * * * *